(12) United States Patent
Oshima et al.

(10) Patent No.: US 11,013,643 B2
(45) Date of Patent: May 25, 2021

(54) DISPOSABLE DIAPER

(71) Applicant: DAIO PAPER CORPORATION, Ehime (JP)

(72) Inventors: Aya Oshima, Tochigi (JP); Aya Takahashi, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 327 days.

(21) Appl. No.: 16/080,065

(22) PCT Filed: Feb. 24, 2017

(86) PCT No.: PCT/JP2017/006997
§ 371 (c)(1),
(2) Date: Aug. 27, 2018

(87) PCT Pub. No.: WO2017/150358
PCT Pub. Date: Sep. 8, 2017

(65) Prior Publication Data
US 2019/0060140 A1 Feb. 28, 2019

(30) Foreign Application Priority Data
Feb. 29, 2016 (JP) .............................. JP2016-037965

(51) Int. Cl.
*A61F 13/15* (2006.01)
*A61F 13/53* (2006.01)
(Continued)

(52) U.S. Cl.
CPC ........ *A61F 13/53* (2013.01); *A61F 13/15731* (2013.01); *A61F 13/49007* (2013.01);
(Continued)

(58) Field of Classification Search
CPC .... A61F 13/532; A61F 13/533; A61F 13/534; A61F 13/511; A61F 2013/530029;
(Continued)

(56) References Cited

U.S. PATENT DOCUMENTS 4,950,264 A * 8/1990 Osborn, III ....... A61F 13/15203
604/385.08
6,563,013 B1 * 5/2003 Murota ............... A61F 13/4704
604/379
(Continued)

FOREIGN PATENT DOCUMENTS

AU 2013342428 12/2017
EP 1774935 4/2007
(Continued)

OTHER PUBLICATIONS

Extended European search report for European Patent Application No. 17759824.0 dated Feb. 18, 2019.
(Continued)

*Primary Examiner* — Jacqueline F Stephens
(74) *Attorney, Agent, or Firm* — IPUSA, PLLC

(57) ABSTRACT

[Technical problem]
A disposable diaper having excellent performances in both the absorbable capacity and the absorption rate, is provided.
[Solution to problem]
The above problem is solved by a pad type disposable diaper 200, in which a top sheet 22 is formed of a thermoplastic nonwoven fabric, and absorbent bodies 23A and 23B are formed of a lower layer absorbent body 23B and an upper layer absorbent body 23A provided on a front surface of the lower layer absorbent body 23B, wherein a slit 40 having a predetermined width is provided in the upper layer absorbent body 23A at least at a crotch portion C2 so as to extend in a front-back direction, and the slit 40 having the predetermined width is not provided in the lower layer absorbent
(Continued)

body 23B, the top sheet 22 includes a depressed portion 30 that is depressed into the slit 40, and multiple low permeation portions 80 are provided with intervals at least in the depressed portion 30, the low permeation portions 80 being portions in which fibers are welded to each other in a state of being compressed in a thickness direction.

7 Claims, 25 Drawing Sheets

(51) Int. Cl.
  *A61F 13/532*     (2006.01)
  *A61F 13/534*     (2006.01)
  *A61F 13/533*     (2006.01)
  *A61F 13/511*     (2006.01)
  *A61F 13/49*      (2006.01)
  *A61F 13/494*     (2006.01)
  *A61F 13/537*     (2006.01)
(52) U.S. Cl.
  CPC .. *A61F 13/49426* (2013.01); *A61F 13/51104* (2013.01); *A61F 13/532* (2013.01); *A61F 13/533* (2013.01); *A61F 13/534* (2013.01); *A61F 13/511* (2013.01); *A61F 2013/530029* (2013.01); *A61F 2013/53035* (2013.01); *A61F 2013/530036* (2013.01); *A61F 2013/53445* (2013.01); *A61F 2013/53778* (2013.01)
(58) Field of Classification Search
  CPC .. A61F 2013/53445; A61F 2013/53778; A61F 2013/53035
  USPC .............................. 604/378, 379, 380, 385.01
  See application file for complete search history.

(56) References Cited

U.S. PATENT DOCUMENTS

| | | | |
|---|---|---|---|
| 2004/0243078 | A1 | 12/2004 | Guidotti et al. |
| 2014/0163511 | A1* | 6/2014 | Roe .................... A61F 13/4756 604/385.101 |
| 2015/0224000 | A1 | 8/2015 | Ota et al. |
| 2016/0250084 | A1 | 9/2016 | Umemoto et al. |
| 2017/0014280 | A1 | 1/2017 | Moritani |
| 2017/0135869 | A1 | 5/2017 | Moriya et al. |

FOREIGN PATENT DOCUMENTS

| | | |
|---|---|---|
| JP | 2013-154016 | 8/2013 |
| JP | 2013-255557 | 12/2013 |
| JP | 2014-046021 | 3/2014 |
| JP | 2015-044046 | 3/2015 |
| JP | 2015-089382 | 5/2015 |
| JP | 2015-188453 | 11/2015 |
| JP | 2016-013209 | 1/2016 |
| WO | 2014/050310 | 4/2014 |
| WO | 2014/073637 | 5/2014 |
| WO | 2016/013448 | 1/2016 |

OTHER PUBLICATIONS

International Search Report for PCT/JP2017/006997 dated May 30, 2017.

* cited by examiner (a)

(b)

DISPOSABLE DIAPER

TECHNICAL FIELD

The present invention relates to a disposable diaper having excellent performances in both the absorbable capacity and the absorption rate.

BACKGROUND ART

One of the typical absorption performances required for disposable diapers will be the absorbable capacity. Normally, the absorbable capacity is determined according to the purpose of the product. For example, products intended for nighttime use, especially nighttime products for adults, are generally products with high absorbable capacity. In such products, in order to secure the absorbable capacity, the absorbent bodies have an upper and lower two-layer structure.

Another typical absorption performance is the absorption rate. In particular, products with high absorbable capacity need to absorb urine that is quickly excreted in large quantities; however, if the absorption rate is low, leakage tends to occur. One technique for improving the absorption rate in a product having absorbent bodies in an upper and lower two-layer structure, is to provide a slit, which penetrates the absorbent bodies in the thickness direction, extending in the front-back direction so as to include the crotch portion. In this case, the diffusibility of urine in the slit becomes high, and urine can be absorbed directly to the lower absorbent body, so that the absorption rate becomes high.

However, in this case, the slit penetrates the upper layer absorbent body and the lower layer absorbent body, and therefore the absorbable capacity is inevitably decreased. When the absorbable capacity decreases, reversion tends to occur, and therefore it is necessary to prevent reversion as much as possible. Reversion is a phenomenon in which urine, which is once absorbed from the surface of the diaper to the absorbent body inside, is returned to the surface of the diaper again, and if the urine easily returns to the surface, the skin unnecessarily becomes dirty with excrement, and problems such as skin trouble tend to occur.

As one means for reducing the decrease in absorbable capacity, it is conceivable to provide a slit only in the upper layer absorbent body (a slit is not provided in the lower layer absorbent body); however, in this case, the lower layer absorbent body will be present on the lower side of the slit, such that the diffusibility of urine in the slit is low and the absorption tends to be saturated (when absorption saturation occurs on the lower side of the slit, there is almost no absorption path to the lower layer absorbent body), so that the absorption rate decreases compared to the case of providing a slit that penetrates the upper layer absorbent body and the lower layer absorbent body.

That is, in a product in which the absorbent bodies have an upper and lower two-layer structure, when an attempt is made to increase the absorption rate by providing a slit in the absorbent body, it has been difficult to improve both the absorbable capacity and the absorption rate.

CITATION LIST

Patent Literature

[PTL 1]
Japanese Patent No. 5669976

[PTL 2]
Japanese Unexamined Patent Application Publication No. 2013-255557

SUMMARY OF INVENTION

Technical Problem

It is therefore an object of the present invention to provide a disposable diaper having excellent performances in both the absorbable capacity and the absorption rate.

Solution to Problem

The present invention solving the above problem is as follows.

Invention According to Claim 1

A disposable diaper including:
a crotch portion;
a front side portion extending to a front side of the crotch portion;
a back side portion extending to a back side of the crotch portion;
an absorbent body provided in a range including the crotch portion in a front-back direction; and
a top sheet covering a front surface of the absorbent body, wherein
the top sheet is formed of a thermoplastic nonwoven fabric,
the absorbent body is formed of a lower layer absorbent body and an upper layer absorbent body provided on a front surface of the lower layer absorbent body,
a slit having a predetermined width is provided in the upper layer absorbent body at least at the crotch portion so as to extend in the front-back direction, and the slit having the predetermined width is not provided in the lower layer absorbent body,
the top sheet includes a depressed portion that is depressed into the slit, and
multiple low permeation portions are provided with intervals at least in the depressed portion, the low permeation portions being portions that are compressed in a thickness direction and portions where fibers are, welded to each other.

Function and Effect

In the disposable diaper according to the present invention, multiple low permeation portions are formed with intervals in the depressed portion depressed into the slit of the top sheet. The low permeation portions are portions where the nonwoven fabric of the top sheet is compressed in the thickness direction and are portions in which fibers are welded to each other, such that and the liquid permeability is lower than the surroundings, and in this case, the low permeation portions include portions where there are gaps between fibers, thus showing some permeability, and also the low permeation portions that are almost completely filmed and that do not permeate any liquid at all. If multiple low permeation portions as described above are provided in the depressed portion, the permeability in the depressed portion is limited, and the diffusibility is improved accordingly. That is, in the present invention, the slit is provided in the upper layer absorbent body, and the slit is not provided in the lower layer absorbent body, such that the absorption amount is secured as much as possible, while the low permeation portions are diffusely arranged, and therefore diffusibility of urine in the slit becomes high, and as a result, absorption saturation is less likely to occur and the absorption rate is high.

Note that the term "slit" means a penetrating portion on the front and back surfaces of the absorbent body. Furthermore, with respect to the slit, "having a predetermined width" merely means that a concave groove or a slit without a gap width (the side walls opposed to each other are in contact) are not included, and does not mean that the width is constant, and therefore, as long as there is a width, a concave groove or a slit having a width that varies may be included.

Invention According to Claim 2

The disposable diaper according to claim 1, wherein an area ratio of the low permeation portions in the depressed portion is greater than or equal to 4%.

Function and Effect

As is clear from the later-described embodiments, when the area ratio of the low permeation portions in the depressed portion of the top sheet (the ratio of the total area of the low permeation portions located in the depressed portion to the total area of the depressed portion) falls within the above range, the absorption rate can be significantly improved.

Invention According to Claim 3

The disposable diaper according to claim 1 or 2, wherein the low permeation portions, which have a shape elongated in the front-back direction, are intermittently provided in the front-back direction at intervals shorter than a length of each of the low permeation portions in the front-back direction, in the depressed portion.

Function and Effect

The shapes of the low permeation portions can be appropriately determined; however, by adopting such a shape and arrangement, the diffusibility of the urine in the front-back direction can be increased even more.

Invention According to Claim 4

The disposable diaper according to any one of claims 1 to 3, wherein the low permeation portions, which have a shape that continues from a front end to a back end of a region including the low permeation portions, are provided in the depressed portion.

Function and Effect

By adopting such a mode, the diffusibility of the urine in the front-back direction can be increased even more.

Invention According to Claim 5

The disposable diaper according to any one of claims 1 to 4, wherein a plurality of rows of the low permeation portions are provided with intervals in a width direction, at least in the depressed portion.

Function and Effect

By adopting such a mode, the diffusibility of the urine in the front-back direction can be increased even more.

Invention According to Claim 6

The disposable diaper according to any one of claims 1 to 5, wherein the low permeation portions are portions that are welded to a member provided on a back surface of the top sheet, and portions between the low permeation portions are protruding portions that are protruding from a front surface of the top sheet.

Function and Effect

The low permeation portions of the top sheet may be provided in any form; however, it is a preferable mode to fix the top sheet to a member on the back surface and also to form protruding portions on the surface. In particular, if such protruding portions are formed in the depressed portion, even when the crotch portion is sandwiched between the legs of the wearer and contracted to some extent in the width direction and the slit is crushed in the width direction, gaps are maintained around the protruding portions, so that improvement in the diffusibility is not easily inhibited.

Advantageous Effects of Invention

As described above, according to the present invention, effects are attained that the disposable diaper will have excellent performances in both the absorbable capacity and the absorption rate, etc.

DESCRIPTION OF EMBODIMENTS

Figure 1:
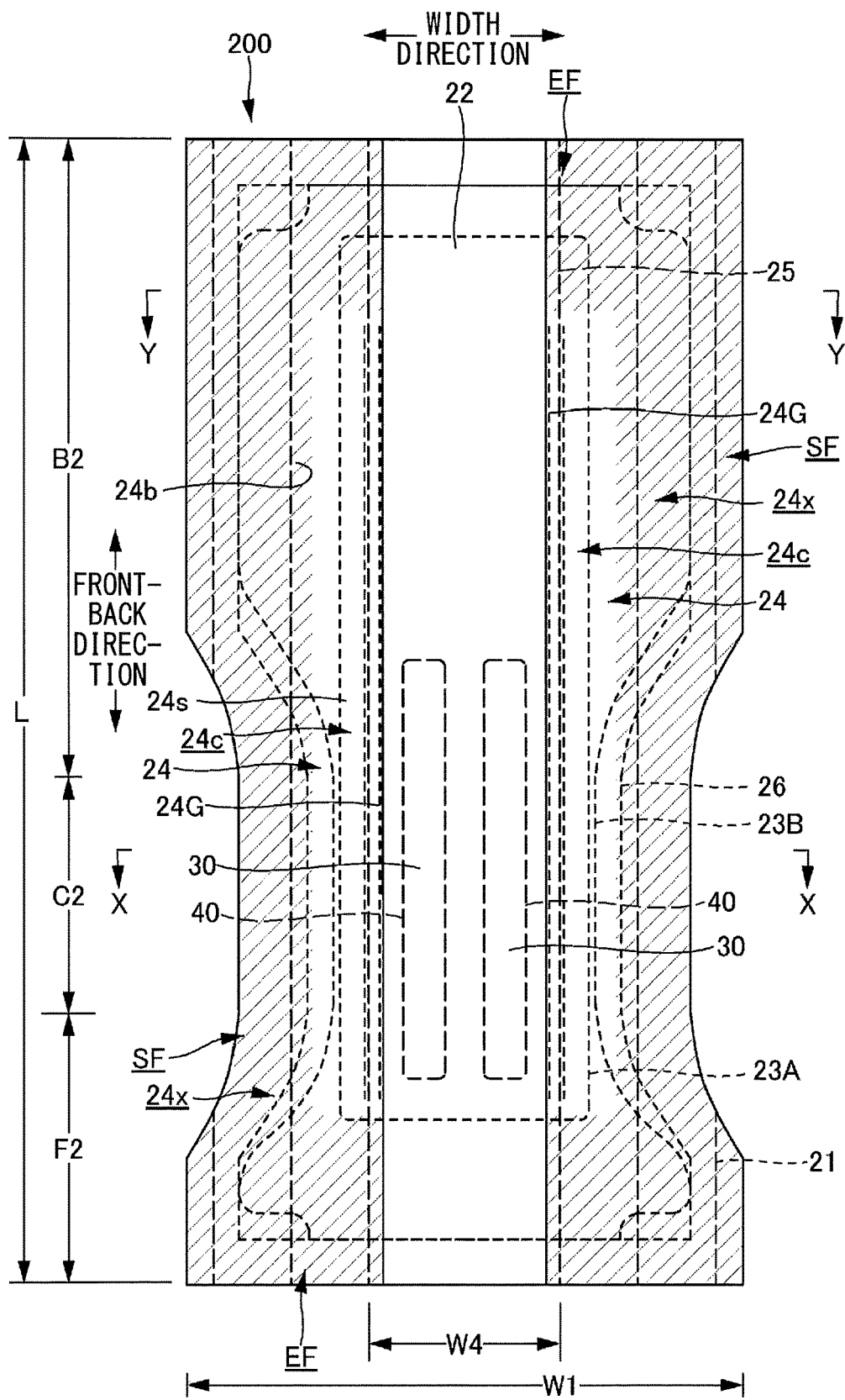
FIG. 1 is a plan view showing an inner surface side of a pad type disposable diaper in an open state.

Hereinafter, an embodiment of the present invention will be described in detail with reference to the accompanying drawings. Note that among the terms of the present invention, the term "crotch portion" means a portion corresponding to the crotch of the body at the time of use, and depending on the product, the crotch portion may be a range from the center in the front-back direction or near the center of an article to a predetermined portion on the front side as in the illustrated embodiment, or a predetermined range at the center in the front-back direction of an article. When there is a constricted portion with a narrow width at the center in the front-back direction of an article or at the center in the front-back direction of an absorbent body, the crotch portion means a predetermined range in the front-back direction with the narrowest portion of one of or both of the constricted portions as the center in the front-back direction. Furthermore, a "front side portion (ventral side portion)" means a portion on the front side than the crotch portion, and "back side portion (back side portion)" means a portion on the back side than the crotch portion.

FIGS. 1 to 4 illustrate a pad type disposable diaper 200 according to the present invention. This pad type disposable diaper 200 has a crotch portion C2 and a front side portion F2 and a back side portion B2 extending on the front and back sides of the crotch portion C2. The sizes of each portion may be defined as appropriate, for example, a total length L (length in front-back direction) of the article may be approximately 350 mm to 700 mm, and a full width W1 may be approximately 130 mm to 400 mm (however, wider than the width of the absorption surface of the diaper); in this case, the length of the crotch portion C2 in the front-back direction may be approximately 10 mm to 150 mm, the length of the front side portion F2 in the front-back direction may be approximately 50 mm to 350 mm, and the length in the front-back direction of the back side portion B2 may be approximately 50 mm to 350 mm. Furthermore, a width W3 of the crotch portion C2 may be 150 cm or more, particularly approximately 200 cm to 260 cm, for adult use.

The pad type disposable diaper 200 has a basic structure in which absorbent bodies 23A and 23B are interposed between the inner surface of a liquid impermeable sheet 21 having an exterior sheet 27 laminated on the outer surface, and a liquid permeable top sheet 22.

On the back side of the absorbent bodies 23A and 23B, the liquid impermeable sheet 21 is provided so as to protrude slightly from the periphery of the absorbent bodies 23A and 23B. As the liquid impermeable sheet 21, other than a polyethylene film, etc., a sheet having moisture permeability without impairing the water shielding property from the viewpoint of prevention of stuffiness, may also be used. As this water shielding/moisture permeable sheet, a microporous sheet may be used, which is obtained by melt-kneading an inorganic filler in olefin resin such as polyethylene or polypropylene, etc., to form a sheet, and then stretching the sheet in a uniaxial direction or biaxial direction.

Furthermore, the outer surface of the liquid impermeable sheet 21 is covered with the exterior sheet 27 made of a nonwoven fabric, and the exterior sheet 27 protrudes to the outside from the periphery of the liquid impermeable sheet 21 with a predetermined protruding width. As the exterior sheet 27, various types of nonwoven fabrics may be used. As the raw material fiber constituting the nonwoven fabric, not only synthetic fibers such as an olefin-based fiber, a polyester-based fiber, and an amide-based fiber, etc., such as polyethylene or polypropylene, but regenerated fiber such as rayon and cupra, etc., and natural fiber such as cotton may be used.

The front side of the absorbent bodies 23A and 23B is covered with the liquid permeable top sheet 22. In the illustrated embodiment, the absorbent bodies 23A and 23B partially protrude from the side edges of the top sheet 22; however, the width of the top sheet 22 may be expanded so that the side edges of the absorbent bodies 23A and 23B do not protrude. As the top sheet 22, a porous or nonporous nonwoven fabric or a porous plastic sheet, etc., is used. As the raw material fiber constituting the nonwoven fabric, not only synthetic fibers such as an olefin-based fiber, a polyester-based fiber, and an amide-based fiber, etc., such as polyethylene or polypropylene, but regenerated fiber such as rayon and cupra, etc., and natural fiber such as cotton may be used.

Between the top sheet 22 and the absorbent bodies 23A and 23B, it is desirable to interpose an intermediate sheet 25. The intermediate sheet 25 is provided to prevent the urine absorbed by the absorbent bodies 23A and 23B from reversing, and the intermediate sheet 25 is preferably made of a material having low water retentivity and high liquid permeability, such as various kinds of nonwoven fabrics and a mesh film, etc. Assuming the front end of the top sheet 22 is set as 0% and the back end of the top sheet 22 is set as 100%, the front end of the intermediate sheet 25 is preferably positioned in the range of 0% to 11%, and the back end of the intermediate sheet 25 is preferably positioned in the range of 92% to 100%. Furthermore, a width W4 of the intermediate sheet 25 is preferably approximately 50% to 100% of a minimum width W5 of a constricted portion 23n of the absorbent bodies 23A and 23B to be described later.

At both end portions in the front-back direction of the pad type disposable diaper 200, the exterior sheet 27 and the liquid permeable top sheet 22 are extended to the front and back sides from the front and back ends of the absorbent bodies 23A and 23B and are adhered to each other, thereby forming an end flap portion EF where the absorbent bodies 23A and 23B do not exist. On both side portions of the pad type disposable diaper 200, the exterior sheet 27 extends outwardly than the side edges of the absorbent bodies 23A and 23B, and on the inner surface of the portion from the extending portion to the side portion of the top sheet 22, a portion 24x on the outer side in the width direction of a gather sheet 24s forming a three-dimensional gather 24, is adhered over the entire front-back direction, thereby forming a side flap portion SF where the absorbent bodies 23A and 23B do not exist. These adhering portions are indicated by an oblique line pattern in FIG. 1, and may be formed by a hot melt adhesive, a heat seal, and an ultrasonic seal. When the exterior sheet 27 is not provided, the liquid impermeable sheet 21 may be extended to the side flap portion SF, instead of the exterior sheet 27, to form the outer surface side of the side flap portion SF.

As the material of the gather sheet 24s, a plastic sheet or a melt-blown nonwoven fabric may be used; however, from the viewpoint of the feeling on the skin, a nonwoven fabric subjected to a water repellent treatment with silicon, etc., is preferably used.

A portion 24c on the center side in the width direction of the gather sheet 24s extends to the top sheet 22, and at the end portion on the center side in the width direction, an elongated elastic member 24G is fixed with a hot melt adhesive, etc., in an extended state in the front-back direction. As the elongated elastic member 24G, materials that are normally used may be used, such as styrene-based rubber, olefin-based rubber, urethane-based rubber, ester-based rubber, polyurethane, polyethylene, polystyrene, styrene-butadiene, silicon, and polyester, etc., in the form of a thread, a string, or a band, etc.

Furthermore, in both of the gather sheets 24s, the portion 24x on the outer side in the width direction is adhered and fixed to the inner surface of the article (in the illustrated embodiment, the surface of the top sheet 22 and the inner surface of the exterior sheet 27) over the entire front-back direction, and the portion 24c on the center side in the width direction is adhered and fixed to the inner surface of the article (in the illustrated embodiment, the surface of the top sheet 22) at both end portions in the front-back direction but is not fixed to the inner surface of the article (in the illustrated embodiment, the surface of the top sheet 22) in between both ends in the front-back direction. As illustrated in FIG. 1, this non-fixed portion is the portion to be a leakage prevention wall that elastically rises with respect to the inner surface of the article (in the illustrated embodiment, the surface of the top sheet 22), and an upright base end 24b of this non-fixed portion is positioned at the boundary between the fixed portion 24x on the outer side and the portion 24c on the inner side in the width direction of the gather sheet 24s.

As illustrated in FIGS. 3 to 6, the absorbent bodies 23A and 23B have a two-layer structure including the lower layer absorbent body 23B and the upper layer absorbent body 23A provided on the front side of the lower layer absorbent body 23B. As the upper layer absorbent body 23A and the lower layer absorbent body 23B, a base material such as a stacked fiber body of pulp fibers, an aggregate of filaments such as cellulose acetate, etc., or a nonwoven fabric is used, and high-absorbent polymers such as particles, etc., may be mixed and fixed, etc., according to need. The lower layer absorbent body 23B is preferably an accumulation of at least pulp fibers, and particularly preferably a mixed accumulation of pulp fibers and high-absorbent polymer particles. On the other hand, the upper layer absorbent body 23A is preferably a mixed accumulation of pulp fiber and high-absorbent polymer particles.

As high-absorbent polymer particles 23p included in the upper layer absorbent body 23A and the lower layer absorbent body 23B, particles used in this type of absorbent article may be directly used; for example, when high-absorbent polymer particles having the same particle size distribution are used for the upper layer absorbent body 23A and the lower layer absorbent body 23B, in typical cases, it is preferable to use particles having the following features. Specifically, when the particles are sieved (shaking for 5 minutes) by using a standard sieve of 500 µm (JIS Z8801-1:2006) and the particles dropped by the above sieving are sieved (shaking for 5 minutes) by using a standard sieve of 180 µm (JIS Z8801-1:2006), the proportion of particles remaining on the standard sieve of 500 µm is 30% by weight or less, and the proportion of particles remaining on the standard sieve of 180 µm is 60% by weight or more. Furthermore, in the case where high-absorbent polymer particles having different particle size distributions are used for the upper layer absorbent body 23A and the lower layer absorbent body 23B, it is preferable to use particles having the following features. Specifically, the high-absorbent polymer particles used for the upper layer absorbent body 23A preferably have a particle size distribution such that when sieving is performed by using the above standard sieves of 500 µm and 180 µm, the proportion of particles remaining on a standard sieve of 500 µm is 50% by weight or less and the proportion of particles remaining on a 180 µm standard sieve is 50% by weight or more. Furthermore, the high-absorbent polymer particles used for the lower layer absorbent body 23B preferably have a particle size distribution such that when sieving is performed by using the above standard sieves of 500 µm and 180 µm, the proportion of particles remaining on a standard sieve of 500 µm is 25% by weight or less and the proportion of particles remaining on a 180 µm standard sieve is 70% by weight or more.

The high-absorbent polymer particles are not particularly limited; however, particles having a water absorption rate of 20 seconds to 50 seconds and a water absorption amount of 50 g/g to 80 g/g may be suitably used. Examples of high-absorbent polymer particles 18p and 19p include starch-based particles, cellulose-based particles, and synthetic polymer-based particles, and a starch-acrylic acid (salt) graft copolymer, a saponified starch-acrylonitrile copolymer, a cross-linked product of sodium carboxymethylcellulose, and an acrylic acid (salt) polymer, etc., may be used.

The basis weight of the fibers and the basis weight of the high-absorbent polymer particles in the absorbent bodies 23A and 23B may be determined as appropriate; however, it is preferable to set the fiber basis weight to approximately 100 g/m² to 600 g/m², and it is preferable to set the basis weight of the high-absorbent polymer particles to approximately 100 g/m² to 350 g/m² for the entire absorbent body.

In particular, the weight ratio of the high-absorbent polymer particles to the pulp fibers in the upper layer absorbent body 23A is preferably higher than the weight ratio of the high-absorbent polymer particles to the pulp fibers in the lower layer absorbent body 23B. That is, in the absorbent bodies 23A and 23B, a liquid component L of excrement is also supplied to the upper layer absorbent body 23A; however, the liquid component L is more preferentially supplied first to the lower layer absorbent body 23B through a slit 40. Here, if the weight ratio of the high-absorbent polymer particles to the pulp fibers in the lower layer absorbent body 23B is lower than that of the upper layer absorbent body 23A, gel blocking is less likely to occur in the lower layer absorbent body 23B than in the upper layer absorbent body 23A, and the liquid component of excrement diffuses in a wider range in the lower layer absorbent body 23B. Then, after absorbing and saturating at least the lower layer absorbent body 23B, the liquid component absorbed by the lower layer absorbent body 23B is transferred to the upper layer absorbent body 23A by being sucked up, so as to be absorbed and retained by the upper layer absorbent body 23A. At this time, the upper layer absorbent body 23A has a high weight ratio of the high-absorbent polymer particles to the pulp fibers and can absorb and retain a larger amount of liquid, and the lower layer absorbent body 23B preferentially absorbs the liquid first, and therefore absorption capacity remains to the end on the front side (skin side) of the upper layer absorbent body 23A. As a result, properties of preventing reversion are further improved.

Considering such an absorption mechanism, with respect to high-absorbent polymer particles included in the lower layer absorbent body 23B, particles having excellent liquid permeability, specifically, particles having an absorption rate of 20 seconds to 35 seconds and an absorption amount of 50 g/g to 70 g/g are preferable, and with respect to high-absorbent polymer particles included in the lower layer absorbent body 23B, particles having a large absorption amount, specifically, particles having an absorption rate of 60 seconds to 80 seconds and an absorption amount of 50 g/g to 80 g/g are preferable.

Furthermore, when the weight ratio of high-absorbent polymer particles to the pulp fibers in the upper layer absorbent body 23A is higher than the weight ratio of high-absorbent polymer particles to the pulp fibers in the lower layer absorbent body 23B, the weight ratio of high-absorbent polymer particles to the pulp fibers in the upper layer absorbent body 23A and the lower. layer absorbent body 23B can be appropriately defined; however, when the total basis weight (the total of pulp 19$f$ and the high-absorbent polymer particles) of the upper layer absorbent body 23A is 350 g/m$^2$ to 700 g/m$^2$, it is preferable that the weight ratio of the high-absorbent polymer particles to the pulp fibers in the upper layer absorbent body 23A is approximately 55% to 100%, particularly preferably 65% to 90%. Furthermore, when the total basis weight (the total of pulp 18$f$ and the high-absorbent polymer particles) of the lower layer absorbent body 23B is 250 g/m$^2$ to 450 g/m$^2$, the weight ratio of the high-absorbent polymer particles to the pulp fibers in the lower layer absorbent body 23B is preferably approximately 0% to 50%, particularly preferably 30 to 40%.

The upper layer absorbent body 23A and the lower layer absorbent body 23B may be wrapped integrally or individually with a packaging sheet 26 having liquid permeability and liquid retentivity such as crepe paper, etc., according to need, for the purpose of forming a shape and retaining polymer.

The absorbent bodies 23A and 23B extend from the front side portion F2 to the back side portion B2. The upper layer absorbent body 23A may have the same size as the lower layer absorbent body 23B; however, it is preferable that the upper layer absorbent body 23A has an overall length and an overall width that are shorter than those of the lower layer absorbent body 23B, as in the illustrated embodiment. In typical cases, the overall length of the upper layer absorbent body 23A may be approximately 60% to 90% of the total length of the lower layer absorbent body 23B, and the overall width of the upper layer absorbent body 23A may be approximately 60% to 90% of the total width of the lower layer absorbent body 23B.

The shapes of the upper layer absorbent body 23A and the lower layer absorbent body 23B may be appropriately determined, and each of the absorbent bodies 23A and 23B may be rectangular; however, at least the larger one of the absorbent bodies 23A and 23B (the lower layer absorbent body 23B in the illustrated example) is preferably formed to have the constricted portion 23$n$ corresponding to a predetermined portion having a narrow width at the center in the front-back direction including the crotch portion C2. The minimum width W5 of the constricted portion 23$n$ is preferably approximately 50% to 65% of the width W2 of the non-constricted portions positioned in front of and behind the constricted portion 23$n$. Furthermore, assuming the front end of the article is set as 0% and the back end of the article is set as 100%, the front end of the constricted portion 23$n$ is preferably positioned in the range of 10% to 25%, the back end of the constricted portion 23$n$ is preferably positioned in the range of 40% to 65%, and the portion of the minimum width W5 of the constricted portion 23$n$ (minimum width portion) is preferably positioned in the range of 25% to 30%.

Figure 2:
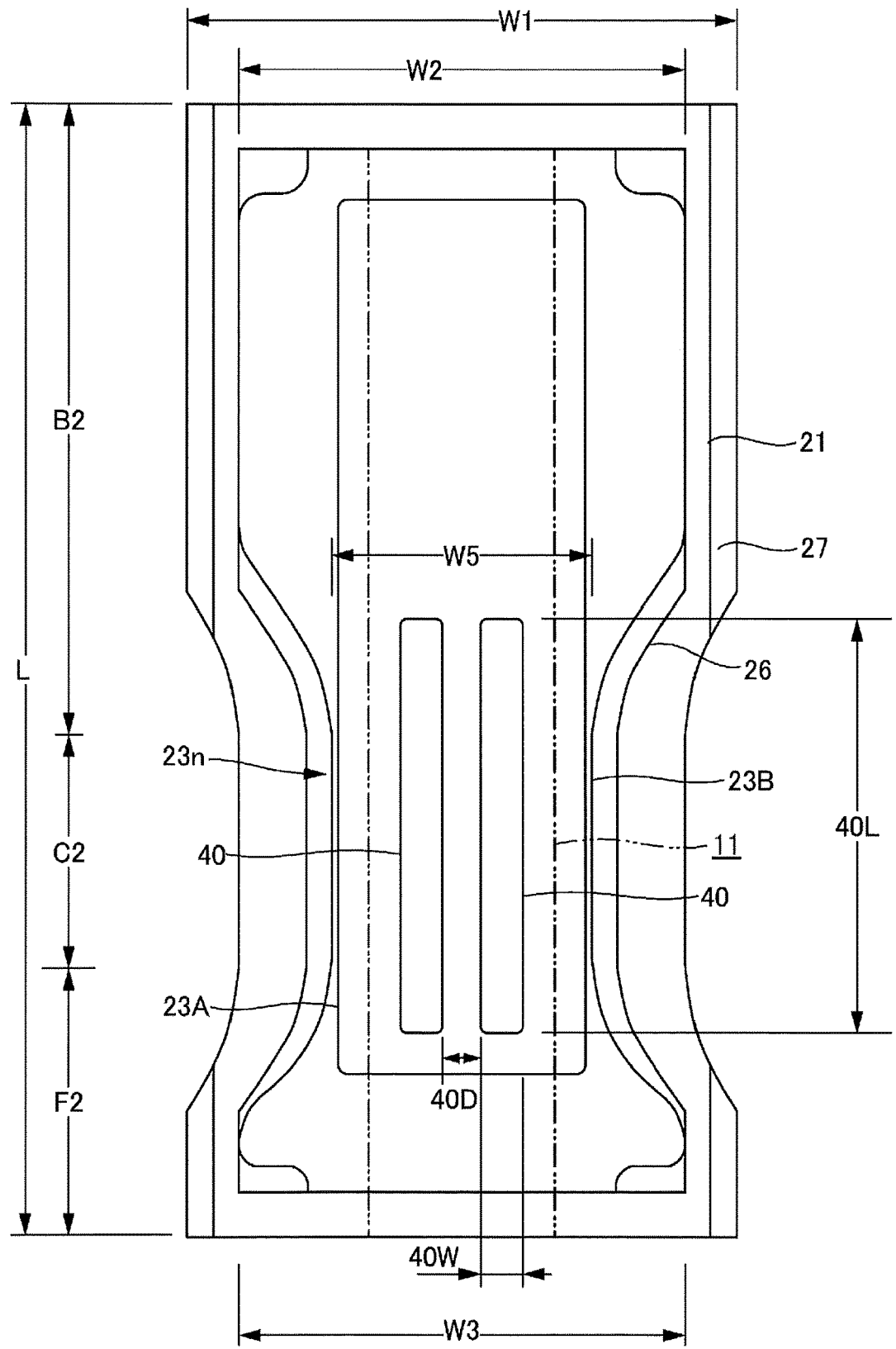
FIG. 2 is a plan view showing only main parts.
Figure 3:
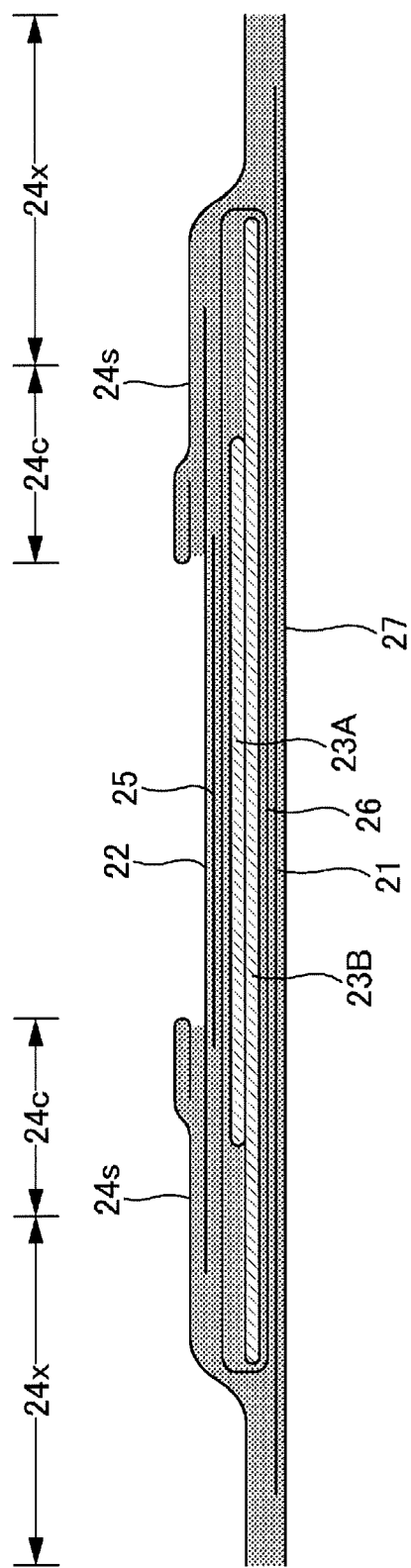
FIG. 3 is a cross-sectional view taken along a line Y-Y in FIG. 1.
Figure 4:
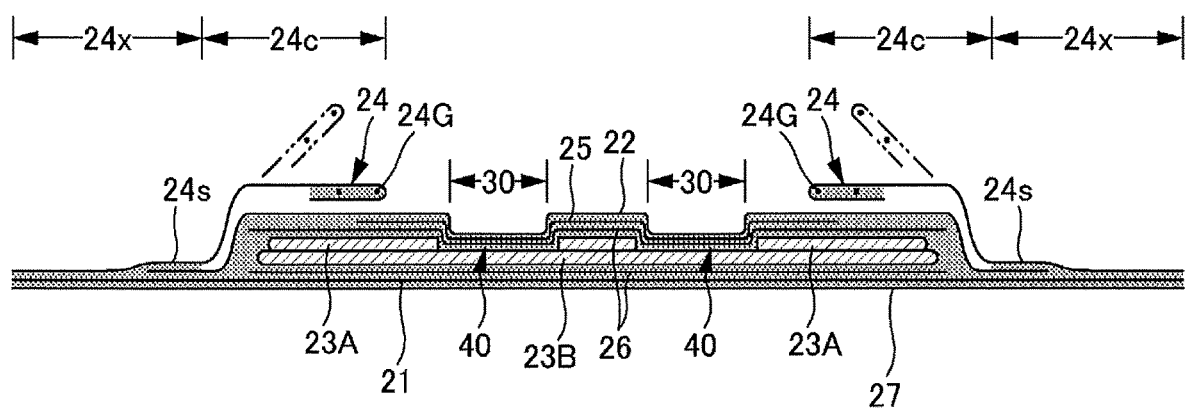
FIG. 4 is a cross-sectional view taken along a line X-X in FIG. 1.
Figure 5:
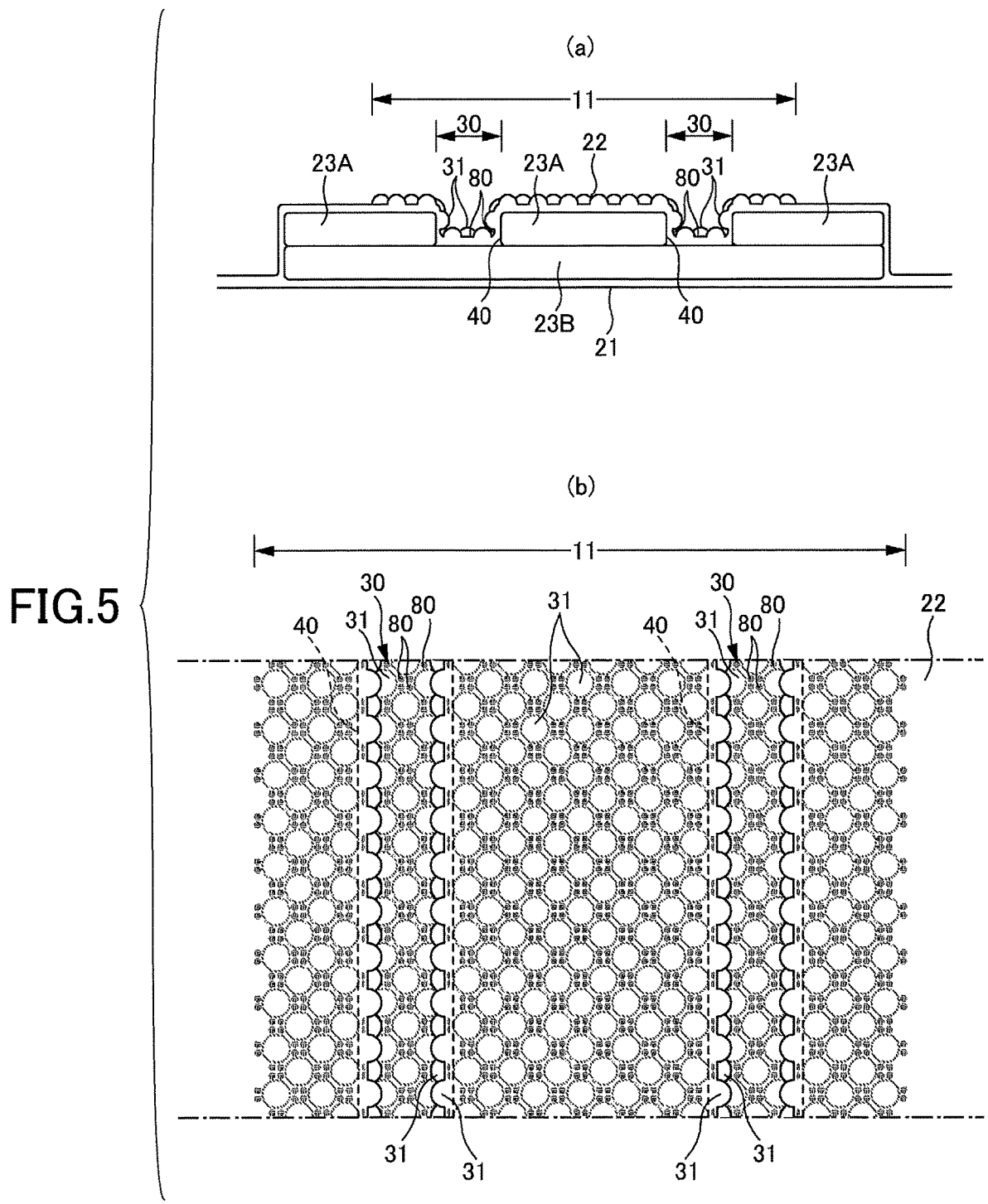
FIG. 5 (*a*) is a schematic cross-sectional view of the open state, and (*b*) is a schematic plan view of the open state.
Figure 6:
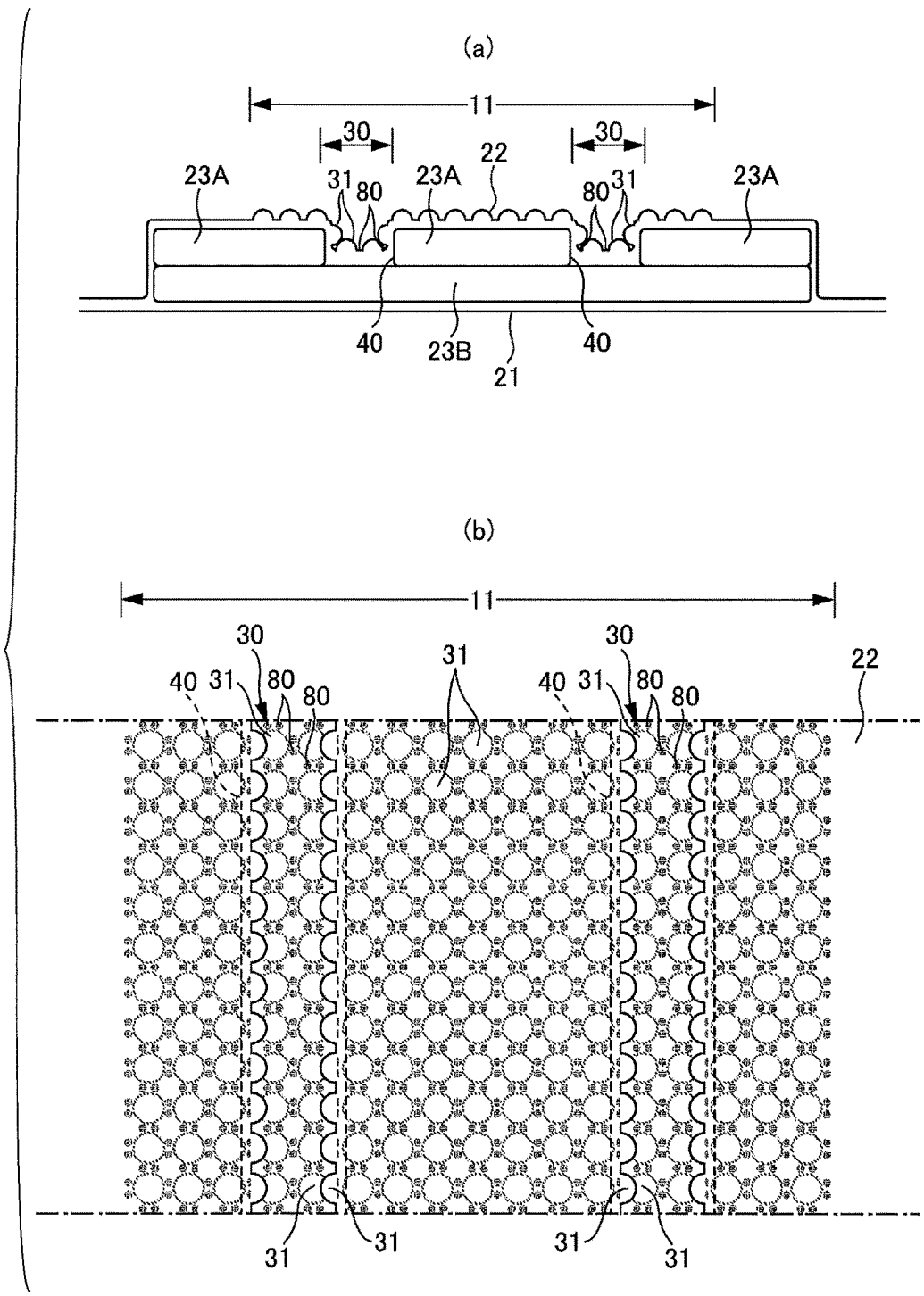
FIG. 6 (*a*) is a schematic cross-sectional view of the open state, and (*b*) is a schematic plan view of the open state.

Characteristically, as illustrated in FIGS. 1 and 2, the slit 40 having a predetermined width extends in the front-back direction in at least the front-back direction region corresponding to the crotch portion C2 in the upper layer absorbent body 23A, but the slit 40 having a predetermined with is not provided in the lower layer absorbent body 23B. However, the lower layer absorbent body 23B may have a notch with no width. Furthermore, characteristically, as illustrated in FIGS. 4 to 6, the top sheet 22 has a depressed portion 30 that is depressed into the slit 40 of the upper layer absorbent body 23A, and as illustrated in FIGS. 5 and 6, at least in this depressed portion 30, a large number of low permeation portions 80, that are portions compressed in the thickness direction and in which fibers are mutually welded, are provided with intervals. In the illustrated embodiment, the front side portions of the intermediate sheet 25 and the packaging sheet 26 exist between the top sheet 22 and the upper layer absorbent body 23A, and therefore the front side portions of the intermediate sheet 25 and the packaging sheet 26 are also depressed in the slit 40 together with the top sheet 22. Elements other than the top sheet 22 may be omitted.

Figure 9:
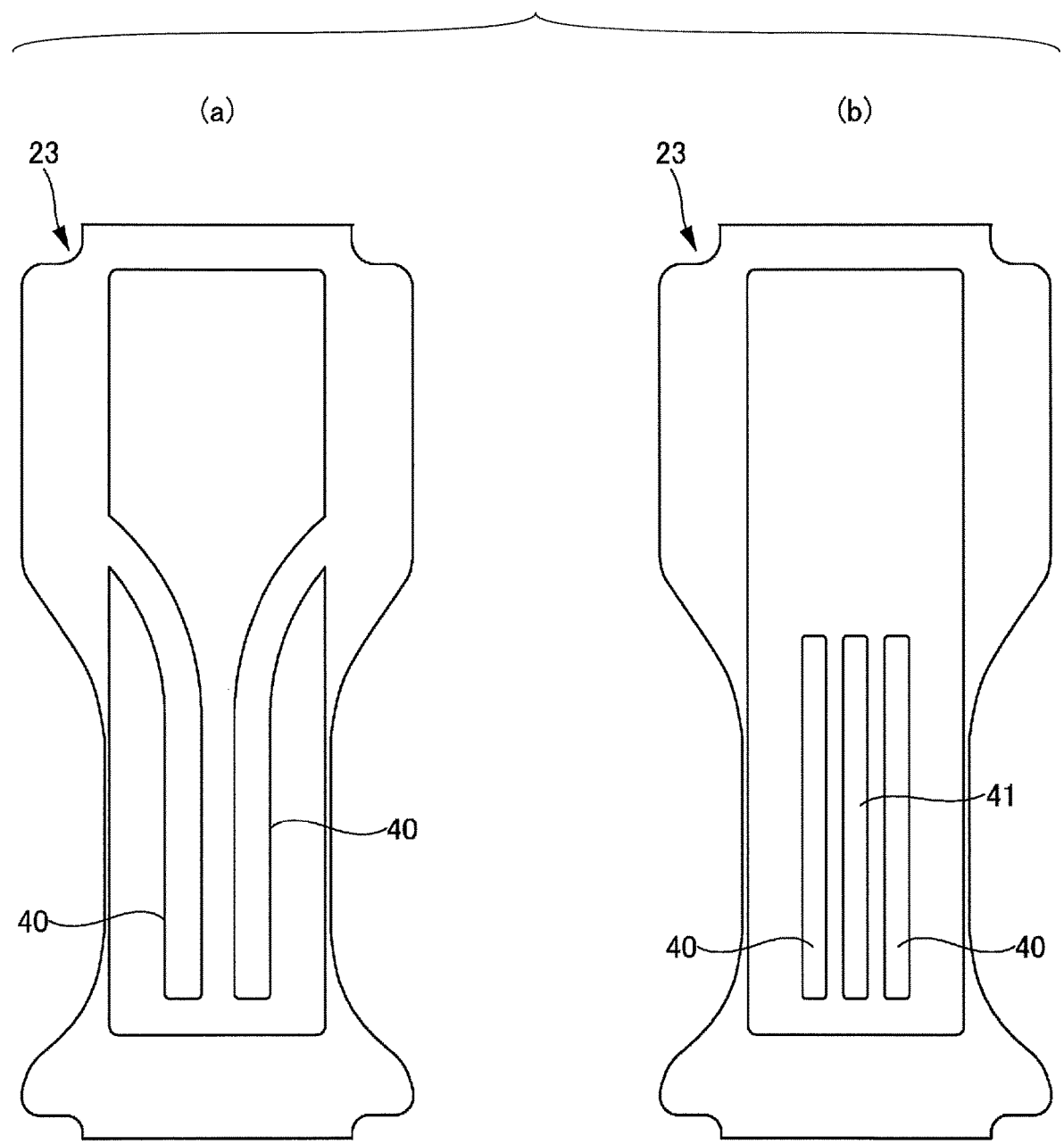
FIG. 9 is a plan view of another absorbent body.

As long as the slit 40 is provided in the crotch portion C2, a length 40L of the slit 40 in the front-back direction is not particularly limited, and therefore the slit 40 may be provided over the entire front-back direction of the upper layer absorbent body 23A; however, as in the illustrated embodiment, the slit 40 preferably extends from the crotch side end portion of the front side portion F2 to the crotch side end portion of the back side portion B2. Furthermore, as illustrated in FIG. 9 ($a$), the back side portion of the slit 40 may be bent so as to face outward in the width direction (the front side may also be bent similarly). More specifically, assuming the front end of the disposable diaper 200 is set as 0% and the back end of the disposable diaper 200 is set as 100%, the front end of the slit 40 is preferably positioned in the range of 15% to 30%, and the back end of the slit 40 is preferably positioned in the range of 40% to 70%.

In the upper layer absorbent body 23A of the illustrated embodiment, the front and back ends of the slit 40 do not penetrate the peripheral edge of the upper layer absorbent body 23A; however, as in the example illustrated in FIG. 9 ($a$), the back end (this may be the front end or both ends) may reach the peripheral edge. Note that in a configuration in which both the front and back ends of the slit 40 reach the side edges of the upper layer absorbent body 23A, the portion closer to the side than the slit 40 is separate from the portion between the slits 40.

Figure 7:
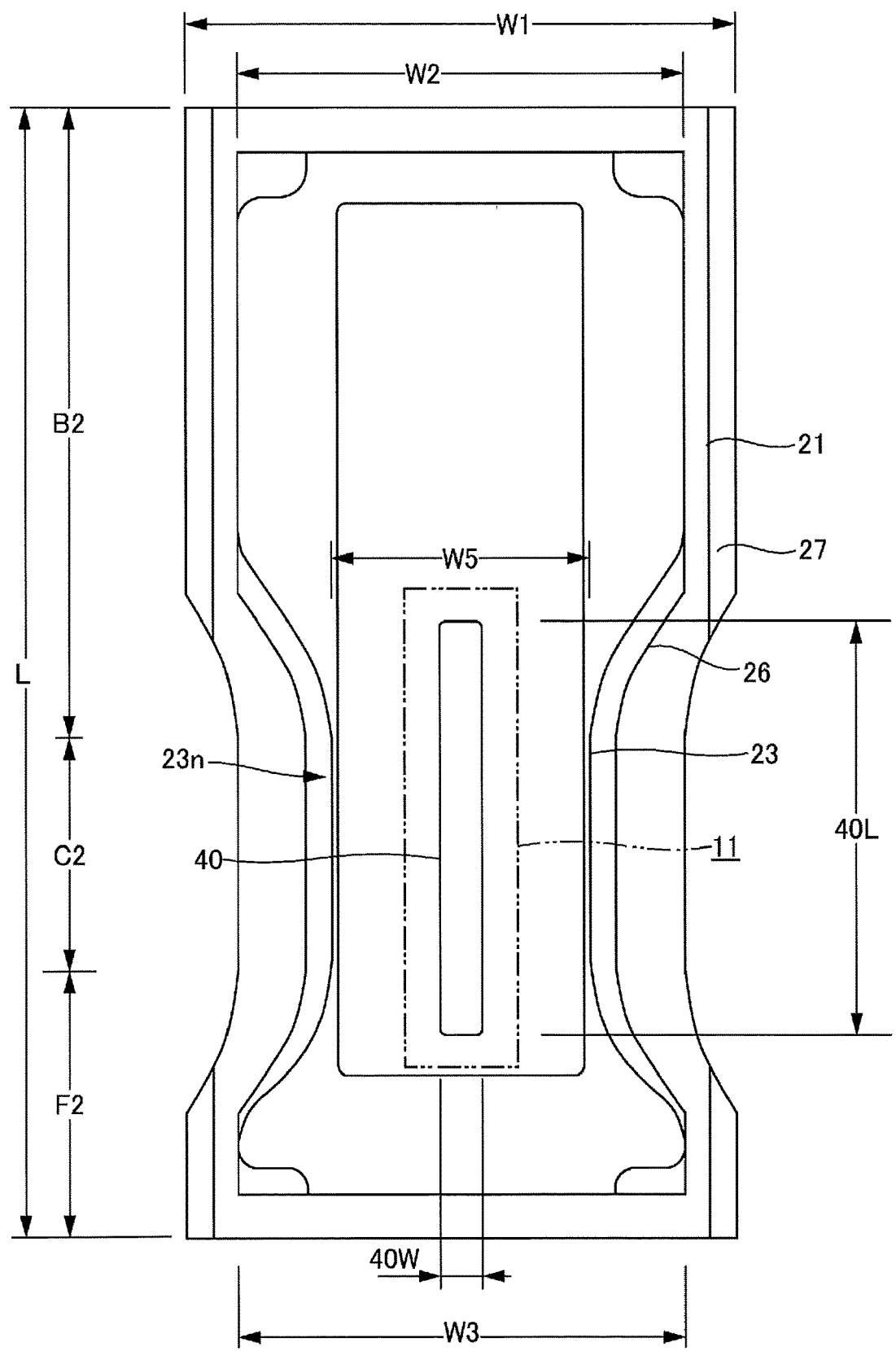
FIG. 7 is a plan view showing only main parts of another embodiment.
Figure 8:
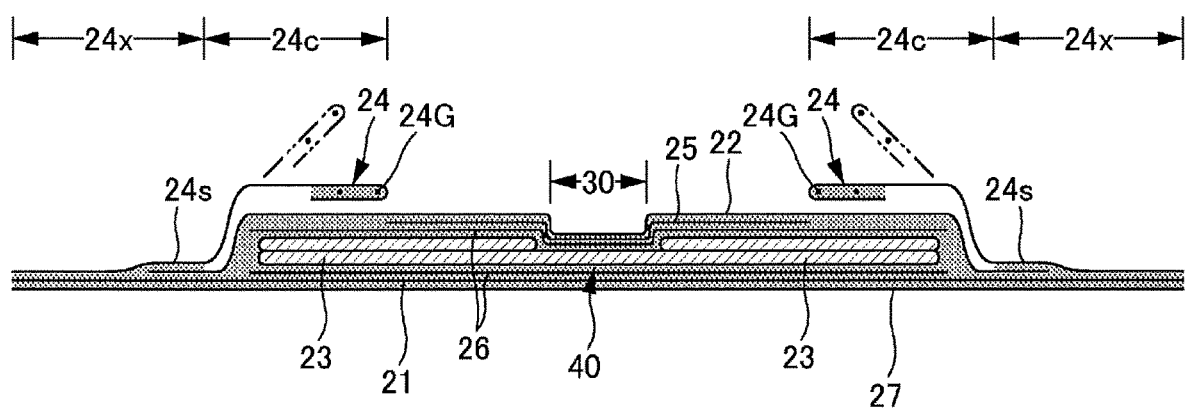
FIG. 8 is a cross-sectional view of another embodiment corresponding to the X-X cross section in the embodiment shown in FIG. 7.

Other than providing one slit 40 on each of the left and right sides, as illustrated in FIG. 9 ($b$), a central slit 41 may be added to the center in the width direction. In this case, it is preferable that the positions of the slits 40 in the width direction are bilaterally symmetric, and in typical cases, an interval 40D between the slits 40 is preferably approximately 10% to 30% of the minimum width W5 of the constricted portion 23n of the absorbent bodies 23A and 23B. The number of the slits 40 is not limited, and as illustrated in FIGS. 7 and 8, only one slit may be provided in the center in the width direction along the front-back direction.

A width 40W of the slit 40 is not particularly limited as long as the opposing side walls are spaced apart from each other. However, in typical cases, the width 40W of the slit 40 is preferably approximately 10% to 20% of the minimum width W5 of the constricted portion 23n of the absorbent bodies 23A and 23B, specifically, the width 40W of the slit 40 may be approximately 5 mm to 32 mm for adult products.

In the pad type disposable diaper 200 configured as described above, as illustrated in FIGS. 5 and 6, a large number of low permeation portions 80 are provided in the depressed portion 30, and therefore the permeability in the depressed portion 30 is limited, and the diffusibility is improved accordingly. That is, although the slit 40 is provided in the upper layer absorbent body 23A and the slit 40 is not provided the lower layer absorbent body 23B so that the absorption amount is secured as much as possible, the low permeation portions 80 are diffusely arranged and thereby the urine diffusivity in the slit 40 becomes high, and as a result, absorption saturation hardly occurs and the absorption rate becomes high.

Although it is possible to appropriately determine how many low permeation portions 80 are to be formed, as is clear from the examples described later, when the area ratio of the low permeation portions 80 in the region including the low permeation portions 80 is 4% or more, it is preferable because the absorption rate can be significantly increased. It is particularly preferable that the area ratio of the low permeation portions 80 in the depressed portion 30 is 7% or more.

Figure 21:
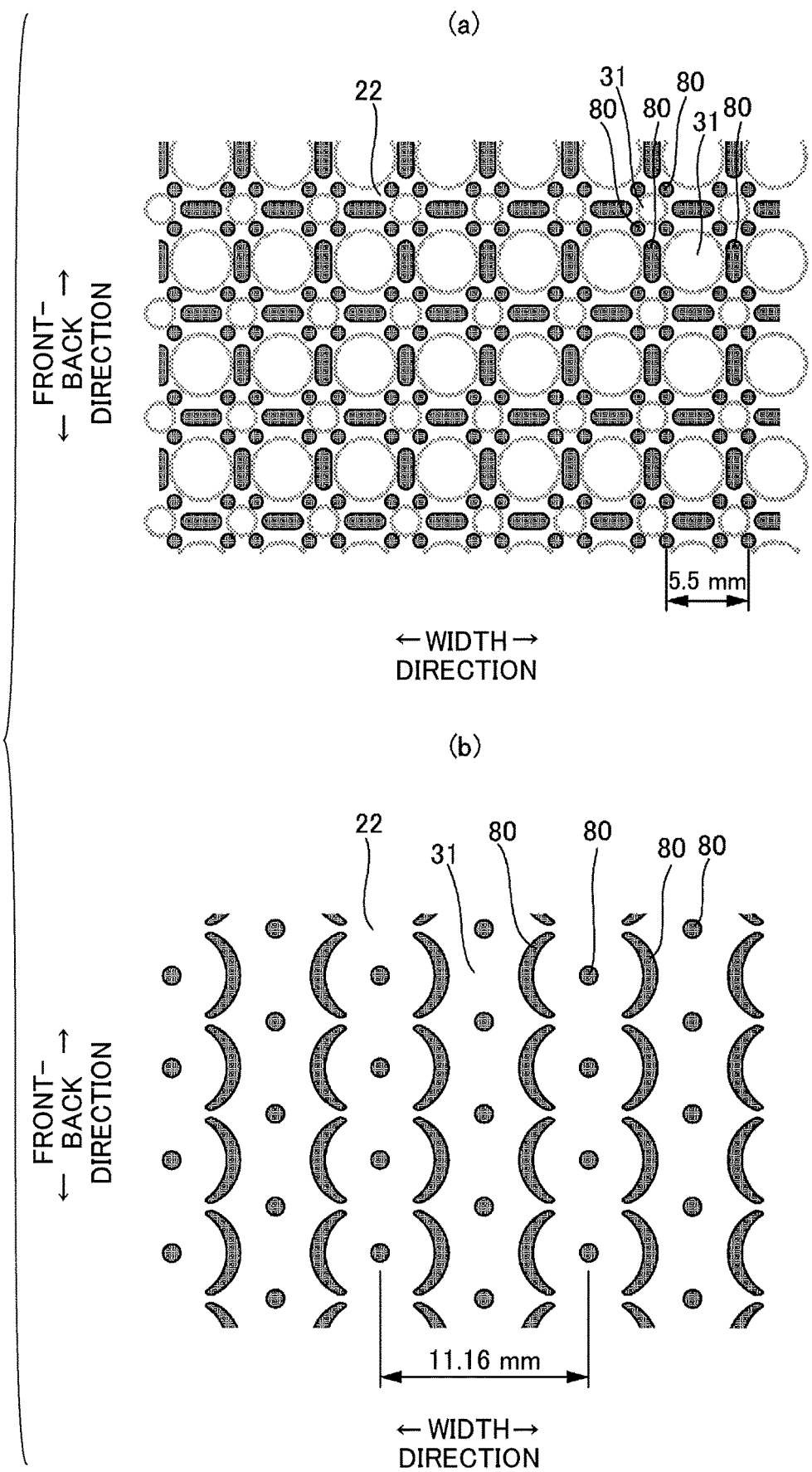
FIG. 21 is an enlarged plan view of a pattern of low permeation portions.

The shape of each of the low permeation portions 80 may be appropriately defined, such as a circular shape (see FIG. 22), an elliptical shape, a square shape, a rectangular shape (see FIG. 21(a)), a linear shape (see FIG. 23), and other shapes such as a polygon, and also a crescent shape (see FIG. 21 (b)), a star shape, and a cloud shape, etc.

The arrangement of the low permeation portions 80 may be determined as appropriate and a configuration may be adopted in which only one row of the low permeation portions 80 intermittently or continuously arranged in the front-back direction, is provided with respect to the depressed portion 30; however, it is preferable that a plurality of rows of the low permeation portions 80 intermittently or continuously arranged in the front-back direction, are formed in the width direction with intervals therebetween and formed at positions shifted or not shifted with respect to each other in the front-back direction. Although the arrangement of the low permeation portions 80 may be irregular, it is preferable that the arrangement is made to be a regular pattern as a whole.

As long as the low permeation portions 80 are provided in the depressed portion 30, the low permeation portions 80 may be provided only in a part of (for example, an intermediate portion in the front-back direction) or in the entirety of the depressed portion 30; however, because it is difficult to manufacture the low permeation portions 80 precisely at the position of the slit 40 of the upper layer absorbent body 23A, as illustrated in FIGS. 5 and 6, the low permeation portions 80 are preferably provided in a region 11 that includes the depressed portion 30 and that is larger than the depressed portion 30 in the top sheet 22 (for example, a region larger than the depressed portion 30 in at least one of the width direction and the front-back direction), or in the entire top sheet 22. When the top sheet 22 is welded and joined to the intermediate sheet 25 at the low permeation portions 80, as illustrated in FIG. 2, it is also preferable to make the region 11 where the low permeation portions 80 are provided match the range of the intermediate sheet 25. In the case of providing a plurality of slits 40 in the width direction with intervals, it is possible to provide a plurality of regions 11 having the low permeation portions 80 in the width direction with intervals, although not illustrated.

The size of the low permeation portion 80 may be defined as appropriate. In the case of intermittently providing the low permeation portions 80 in the front-back direction, the length in the front-back direction (for example, the reference numeral 80m in the embodiment to be described later) may be set to approximately 0.5 mm to 3.0 mm, particularly approximately 0.7 mm to 1.1 mm. In typical cases, the width of the low permeation portion 80 (for example, the reference numeral 80c in the embodiment to be described later) may be set to approximately 0.5 mm to 3.0 mm, particularly approximately 0.7 mm to 1.1 mm. Furthermore, when the low permeation portions 80 are intermittently provided in the front-back direction, the area of each of the low permeation portions 80 may be set to approximately 0.19 mm$^2$ to 7.1 mm$^2$, particularly approximately 0.38 mm$^2$ to 0.95 mm$^2$. Furthermore, in the case where a plurality of rows of the low permeation portions 80 are provided in the width direction, the center interval between the adjacent rows may be larger than the row width, preferably approximately 1 to 5 times larger than the row width, approximately at 0.5 mm to 15 mm in typical cases.

In one preferred embodiment, as illustrated in FIG. 21, the low permeation portions 80 having a shape elongated in the front-back direction are intermittently provided in the front-back direction at intervals shorter than the length in the front-back direction. By adopting such a shape and arrangement, the diffusibility of the urine in the front-back direction becomes even higher.

Figure 23:
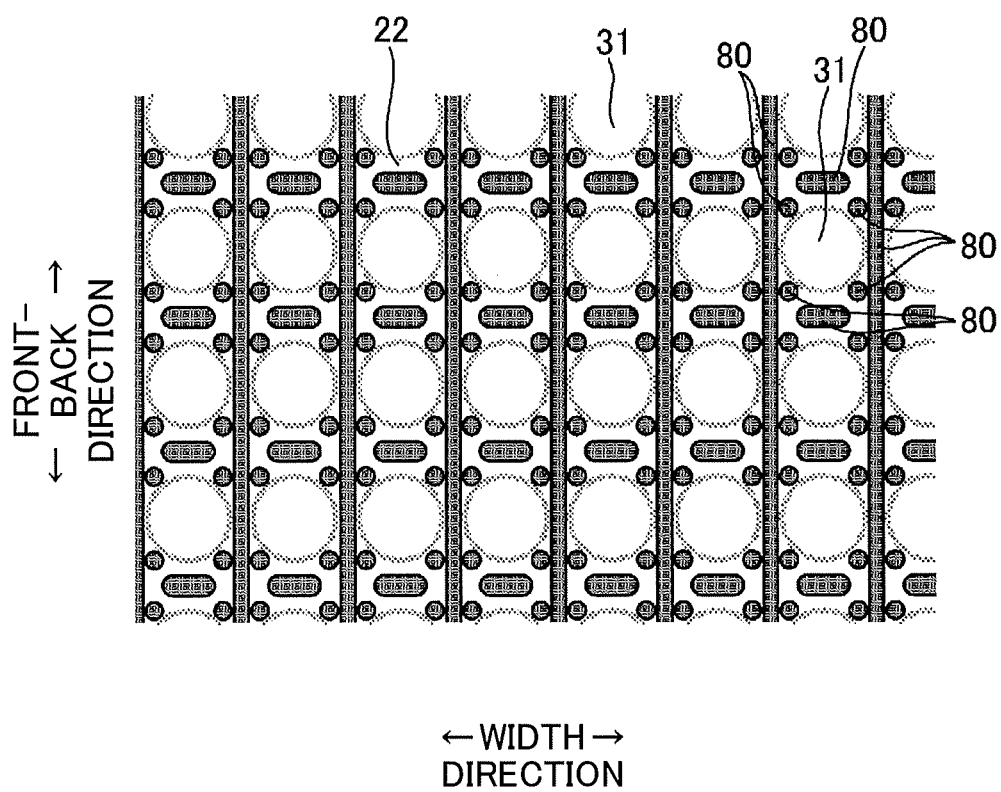
FIG. 23 is an enlarged plan view of a pattern of low permeation portions.

Furthermore, as illustrated in FIG. 23, it is also a preferable embodiment to continuously have the low permeation portions 80 from the front end to the back end of the region 11 including the low permeation portions 80.

The low permeation portions 80 in the top sheet 22 may be formed in any embodiment. For example, by heat-embossing the top sheet 22 individually, etc., an embodiment may be formed such that the low permeation portions 80 are not adhered to a back side member according to the welding of fibers. However, the low permeation portions 80 are where fibers are welded, and therefore it is one preferable embodiment to fix the top sheet 22 to a back side member by using the low permeation portions 80. In this case, the portions between the low permeation portions 80 are not compressed and become protruding portions 31 protruding to the front side, and therefore the protruding portions 31 on the front surface are also formed at the same time. When the protruding portions 31 as described above are formed in the depressed portion 30, even when the crotch portion C2 is sandwiched between the legs of the wearer and contracts to a certain degree in the width direction and the slit 40 is crushed in the width direction, gaps are maintained around the protruding portions 31, so that the improvement of diffusibility is not easily inhibited.

The protruding portions 31 are formed as long as the low permeation portions 80 are relatively compressed with respect to the surroundings and joined to the back side member (in the case of the illustrated embodiment, the intermediate sheet 25), without performing extrusion processing to be described later, and the arrangement, the size, and the shape of the protruding portions 31 can be determined by the arrangement, the size, and the shape of the low permeation portions 80. That is, according to the desired arrangement of the protruding portions 31, it is sufficient to provide the low permeation portions 80 singly or densely packed on at least three sides around the protruding portion 31, and the region including the protruding portions 31 and the region 11 including the low permeation portions are almost the same.

Figure 11:
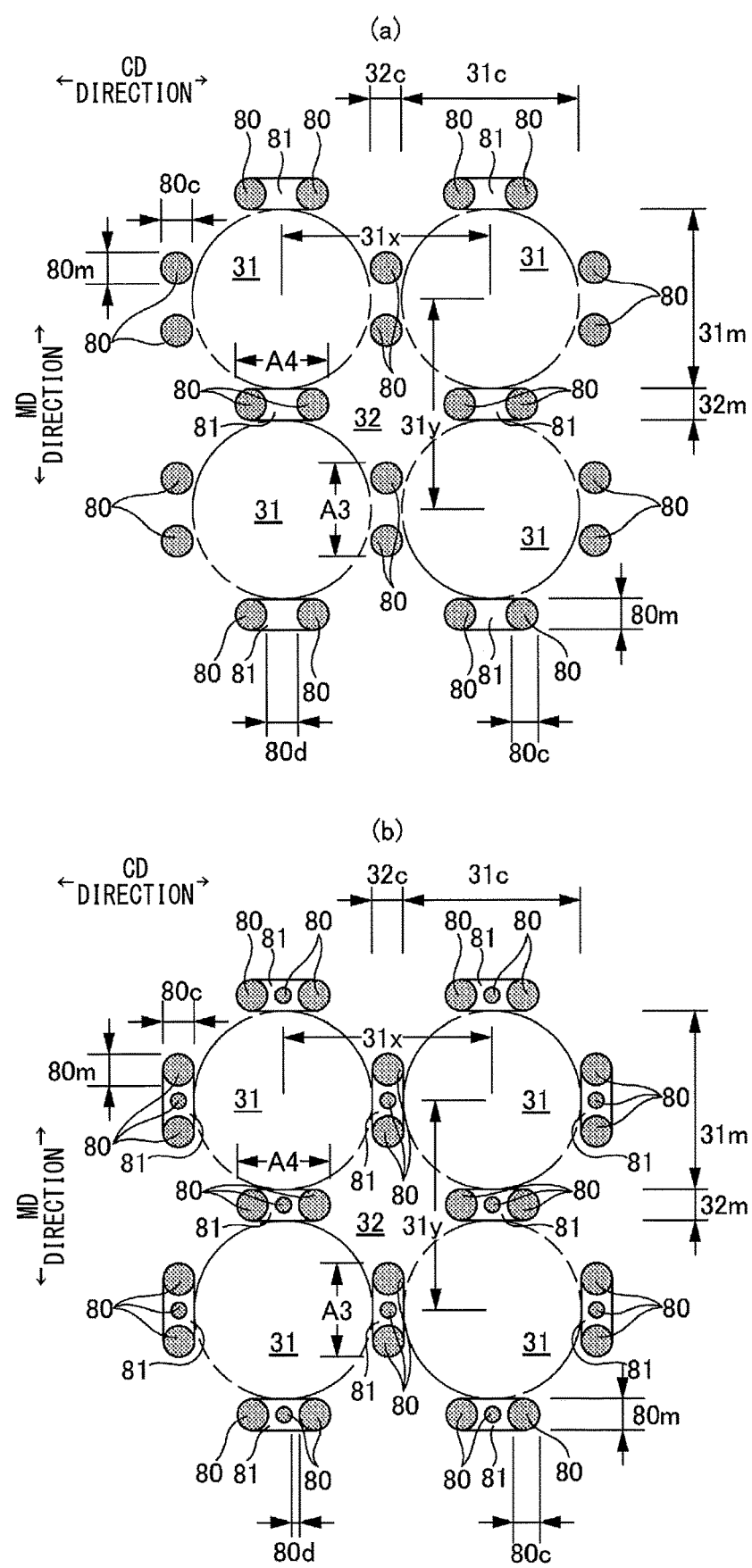
FIG. 11 is an enlarged plan view of a pattern of low permeation portions.
Figure 12:
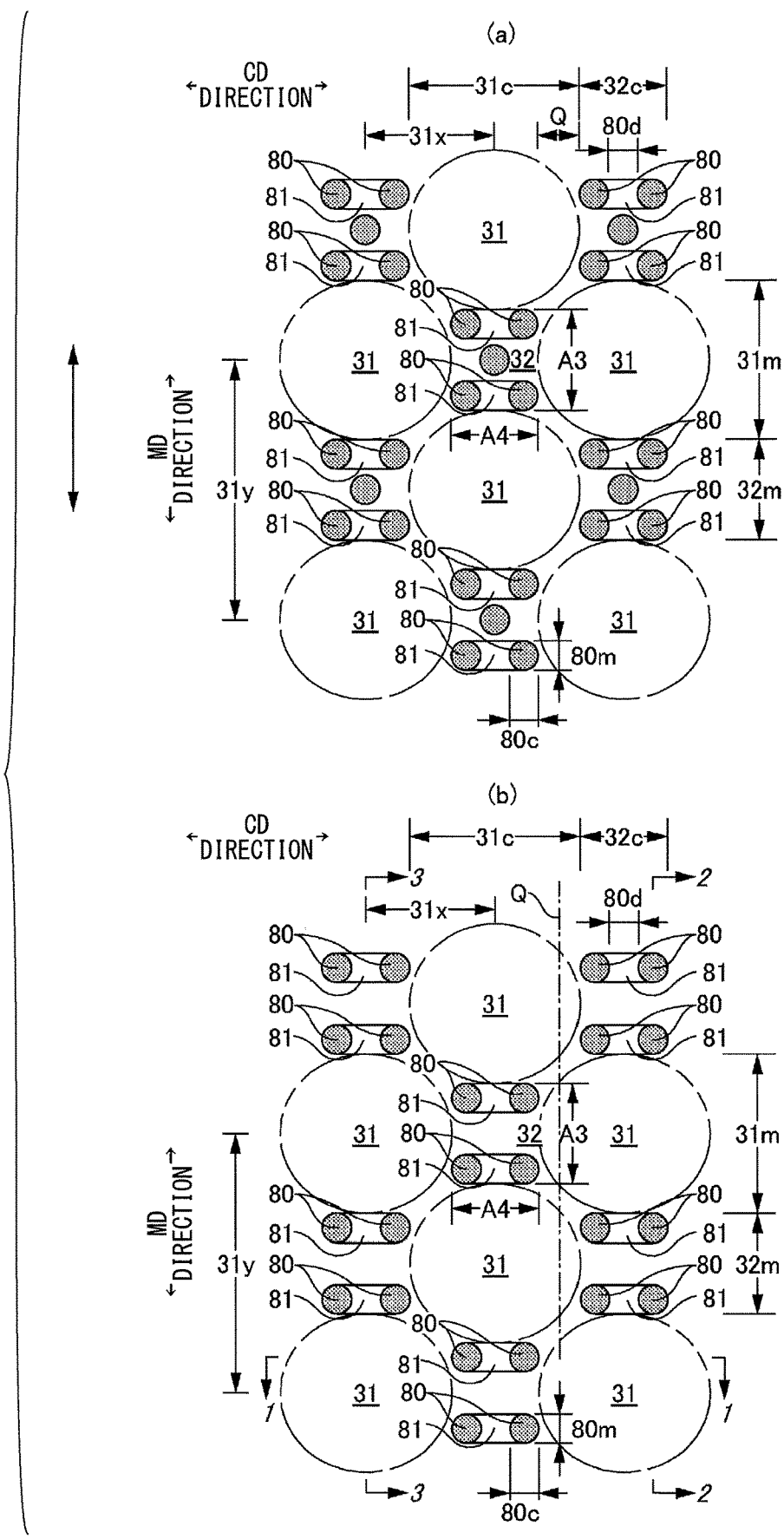
FIG. 12 is an enlarged plan view of a pattern of low permeation portions.
Figure 13:
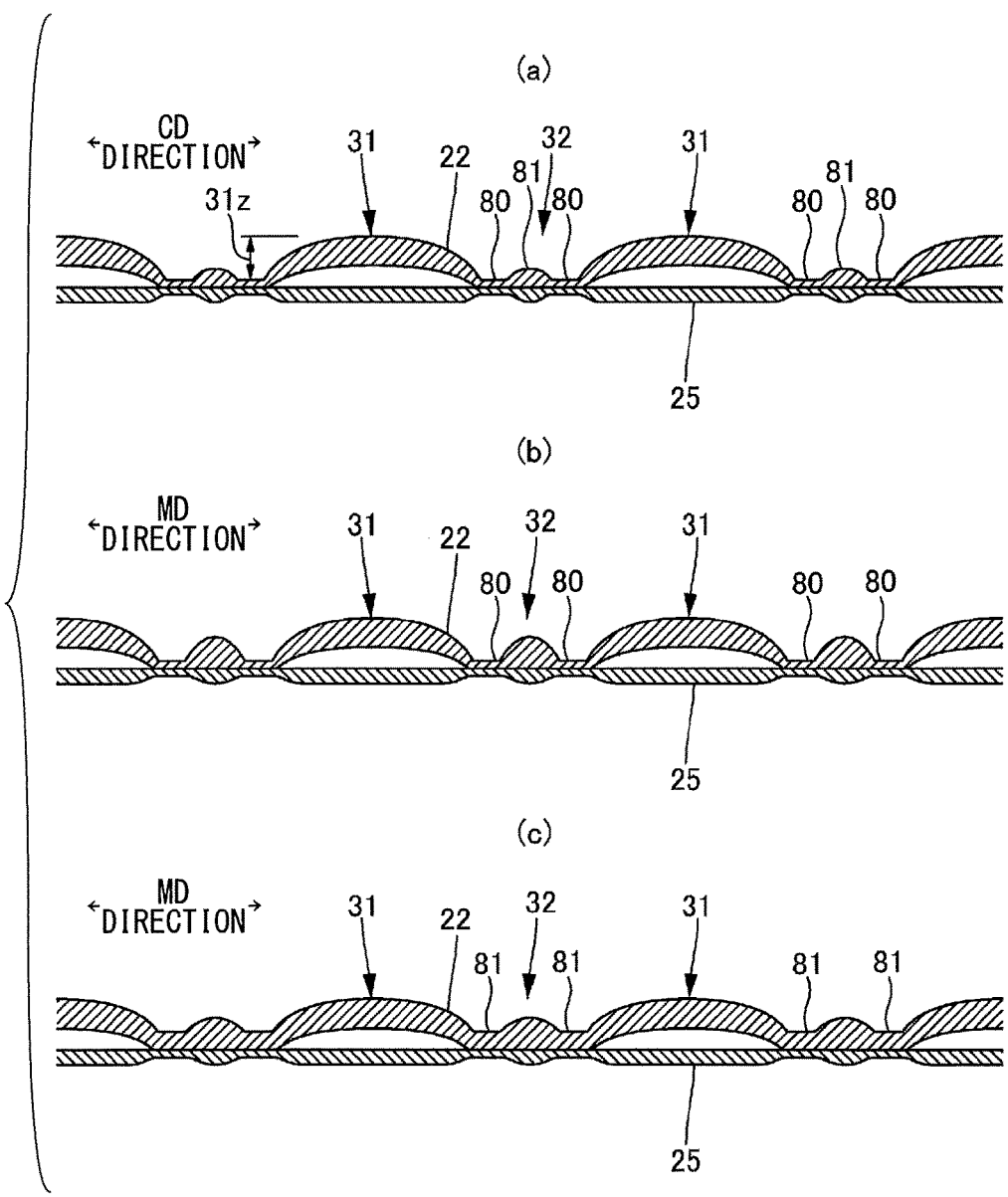
FIG. 13 is a cross-sectional view showing a section 1-1, a section 2-2, and a section 3-3 of FIG. 12 (*b*).

As illustrated in FIGS. 11 and 12, in the case where a large number of protruding portions 31 are arranged with intervals in the width direction and the front-back direction, a size 31m in the front-back direction of the protruding portion 31 is preferably larger than an interval 32m between the protruding portions 31 arranged in the front-back direction. Similarly, it is preferable that a width 31c in the width direction of the protruding portion 31 is larger than an interval 32c between the protruding portions 31 arranged in the width direction. If the sizes 31m and 31c of the protruding portion 31 are small, and the intervals 32m and 32c between the protruding portions 31 are too wide, or the protruding portion 31 has a size that fits into a portion 32 between adjacent protruding portions, the space securing function described above may only be exerted locally. On the other hand, if the sizes 31m and 31c of the protruding portions 31 are larger than the intervals 32m and 32c of the protruding portions 31, the occupying area of the protruding portions 31 is larger than that of intervals between the protruding portions 31. Therefore, regardless of the arrangement, and irrespective of how the depressed portion 30 deforms, the protruding portions 31 on one opposing side surface will not enter between the protruding portions 31 on the other opposing side surface, but the opposing protruding portions 31 each other will contact each other, and therefore a more preferable space securing state is obtained.

As illustrated in FIG. 5, when the protruding portions 31 are arranged in a staggered arrangement, the interval between the protruding portions 31 arranged in the width direction is preferably 0.5 to 0.9 times the size of the protruding portion 31 in the width direction. As also illustrated in FIG. 12, when the protruding portions 31 are arranged in a staggered arrangement, the portion (low-rigidity portion) between the protruding portions 31 continues most in the front-back direction in a linear manner at the center in the width direction of protruding portions 31 arranged in a zigzag manner in the front-back direction, and therefore when the width of the slit 40 becomes narrow, the top sheet 22 bends at this position Q. Here, when the protruding portions 31 are arranged with the above-mentioned sizes and intervals, the protruding portions 31 on one opposing side surface hardly enter between the protruding portions 31 on the other opposing side surface, and the protruding portions 31 opposing each other are likely to contact each other, and therefore a more preferable space securing state is obtained.

Furthermore, as illustrated in FIG. 6, when the protruding portions 31 are arranged in a matrix, the interval 32c between the protruding portions 31 arranged in the width direction is 0.1 to 0.5 times the size 31c of the protruding portions 31 in the width direction. That is, as illustrated in FIG. 11, in the case where the arrangement of the protruding portions 31 is in a matrix form, the portion (low-rigidity portion) between the protruding portions 31 continues most in the front-back direction in a linear manner at the interval 32c between the rows of protruding portions 31 adjacent to each other in the width direction, and therefore when the width of the slit 40 becomes narrow, the top sheet 22 bends at this position 32c. In this case, when the protruding portions 31 are arranged with the above-mentioned sizes 31c and intervals 32c, the protruding portions 31 on one opposing side surface will not enter between the protruding portions 31 on the other opposing side surface, but the protruding portions 31 opposing each other will contact each other, and therefore a more preferable space securing state is obtained.

Specific sizes, shapes, arrangements and structures of the protruding portions 31 of the top sheet 22 are not particularly limited, and can be determined as appropriate. An example is as follows.

Figure 10:
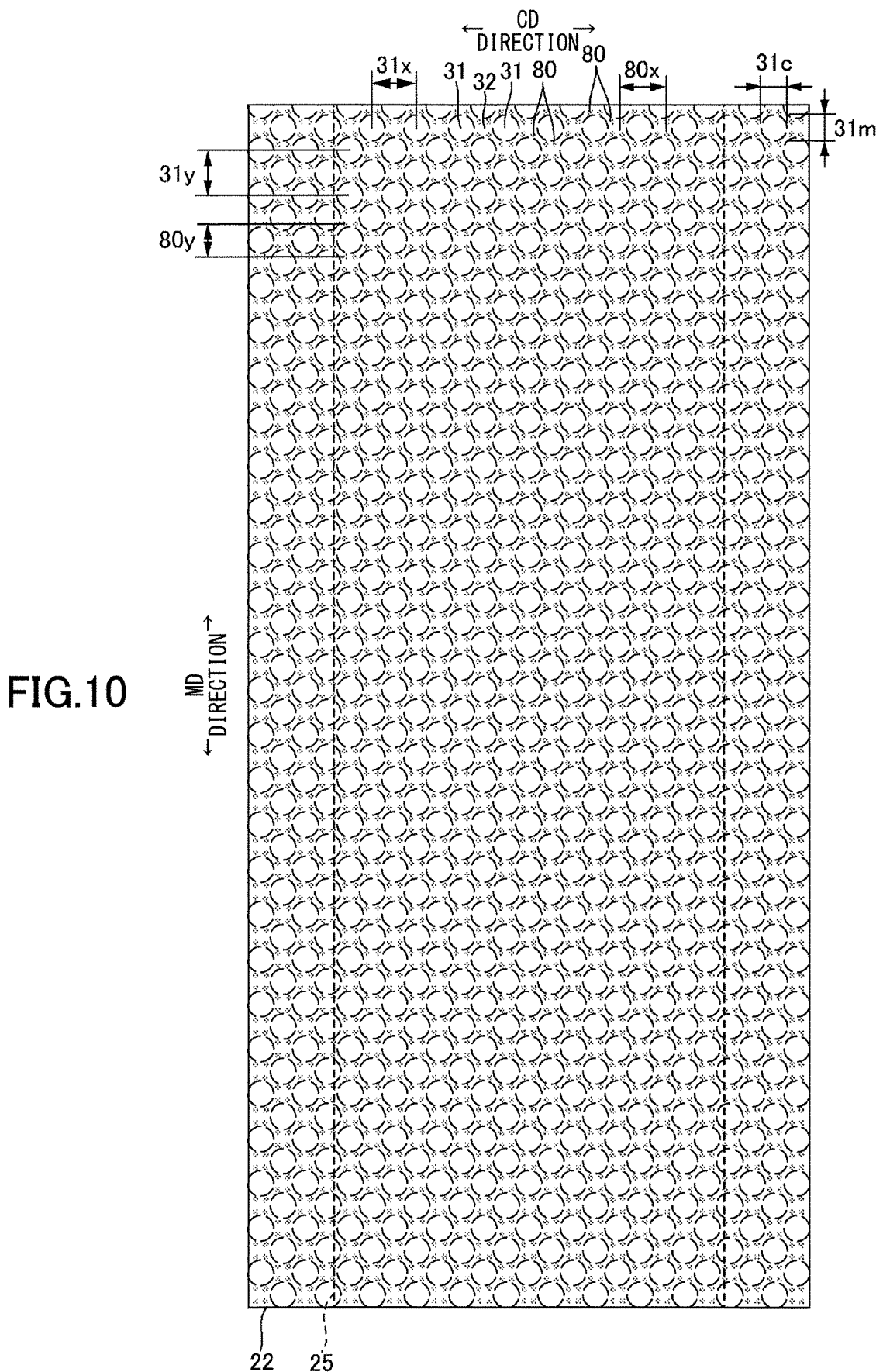
FIG. 10 is a plan view of a top sheet and a second sheet.

That is, as illustrated in FIGS. 10 to 13, by performing extrusion on the top sheet 22 from the back side to the front side by embossing, it is possible to arrange a large number of the protruding portions 31 with intervals in the width direction and the front-back direction. Note that reference numeral 32 indicates a portion between adjacent protruding portions 31. This arrangement mode may be appropriately changed, for example, to a matrix, etc., as illustrated in FIG. 11, and to a staggered arrangement (adjacent rows being alternately arranged) as illustrated in FIGS. 10 and 12. Furthermore, in the illustrated embodiment, it is assumed that the protruding portions 31 are provided over almost the entirety of the top sheet 22, but as long as the protruding portions 31 are provided in at least the depressed portion 30 as described above, the protruding portions 31 may be only provided partially, for example, the protruding portions 31 may be provided in substantially the entire region where the top sheet 22 and the intermediate sheet 25 overlap each other.

The size, etc., of the protruding portions 31 may be appropriately defined; however, as illustrated in FIGS. 10 to 12, the size 31m of the protruding portion 31 in the MD direction is defined as less than or equal to a center interval 80y between the low permeation portion 80 positioned on one side of the protruding portion 31 in the MD direction and the low permeation portion 80 positioned on the other side of the protruding portion 31 in the MD direction, and the lower limit of the size is preferably approximately 0.9 times the size of the center interval 80y, and the size is preferably appropriately 2.7 mm to 9 mm in typical cases. Similarly, the size 31c of the protruding portion 31 in the CD direction is defined as less than or equal to a center interval 80x between the low permeation portion 80 positioned on one side of the protruding portion 31 in the CD direction and the low permeation portion 80 positioned on the other side of the protruding portion 31 in the CD direction, and the lower limit of the size is preferably approximately 0.9 times the size of the center interval 80x, and the size is preferably appropriately 2.7 mm to 9 mm in typical cases. Furthermore, it is preferable that a height 31z of the protruding portion 31 is approximately 0.8 mm to 2 mm in typical cases.

Here, the "MD direction" and "CD direction" in the manufacturing method mean "MD direction" and "CD direction" of the processing facility of the protruding portions 31, and either one is the front-back direction and the other one is the width direction. Furthermore, the MD direction of the product is the direction of the fiber orientation of the nonwoven fabric of the top sheet 22. The fiber orientation is the direction along which the fibers of the nonwoven fabric run; for example, the fiber orientation can be determined by a measurement method according to the fiber orientation test method based on the zero distance tensile strength according to the TAPPI standard method T481 and the simple measurement method for determining the fiber orientation direction based on the tensile strength ratio in the front-back direction and the width direction. In the illustrated embodiment, the front-back direction is the MD direction and the width direction is the CD direction, similar to most disposable diaper products.

The arrangement intervals of the protruding portions 31 may be appropriately defined; however, in the case of the matrix arrangement as illustrated in FIG. 11, the CD direction center interval 31x of the MD direction rows of the protruding portions 31 adjacent to each other in the CD direction, is preferably approximately 3 mm to 10 mm, and the MD direction center interval 31y of the CD direction rows of the protruding portions 31 adjacent to each other in the MD direction, is preferably approximately 3 mm to 10 mm. Furthermore, in the case of the staggered arrangement as illustrated in FIGS. 10 and 12, the CD direction center interval 31x of the MD direction rows of the protruding portions 31 adjacent to each other in the CD direction is preferably approximately 3 mm to 10 mm, and the MD direction center interval 31y of the CD direction rows of the protruding portions 31 adjacent to each other in the MD direction is preferably approximately 3 mm to 10 mm The shape of the protruding portion 31 is preferably a circular dome shape; however, the protruding portion 31 may also have an elliptical dome shape or a regular polygonal dome shape. Note that the protruding portions 31 may be formed by embossing the top sheet 22.

As illustrated in FIGS. 10 to 13, the portions between the protruding portions 31 adjacent to each other in the width direction and the front-back direction in the top sheet 22 are joined to the intermediate sheet 25 by pressure welding, whereby a large number of the low permeation portions 80 are formed in an intermittent pattern in the width direction and the front-back direction. The low permeation portions 80 are also portions forming the bottom parts of recesses. Characteristically, in the joining pattern of the top sheet 22 and the intermediate sheet 25, in a region between the protruding portions 31 adjacent to each other in the MD direction, a row in which a plurality of the low permeation portions 80 are arranged side by side with intervals therebetween in the CD direction is formed so as to traverse a center position in the CD direction of this region, and at the interval portion between the low permeation portions 80 in the CD direction, the top sheet 22 and the intermediate sheet 25 are not welded, thereby forming a compression portion 81 where the top sheet 22 is more compressed than portions on both sides thereof in the MD direction. In the compression portion 81, as long as the top sheet 22 is compressed, the intermediate sheet 25 may be compressed integrally with the top sheet 22 or may not be compressed. Furthermore, at the portions other than the low permeation portions 80 and the compression portions 81, the top sheet 22 and the intermediate sheet 25 may not be welded, and may be compressed similar to the interval portions in the CD direction; however, it is preferable that the top sheet 22 and the intermediate sheet 25 are not welded and that the top sheet 22 is not compressed as much as the interval portions in the CD direction (also including non-compressed portions that are not compressed at all). That is, assuming that the thickness of the low permeation portions 80 in the top sheet 22 is T1, the thickness of the compression portions 81 is T2, and the thickness of the portions other than the low permeation portions 80 and the compression portions 81 is T3, it is acceptable that that T1<T2=T3 is satisfied; however, it is more preferable that T1<T2<T3 is satisfied. Furthermore, in the illustrated embodiment, a space is formed between the portions having the protruding portions 31 in the top sheet 22 and the intermediate sheet 25; however, this space does not need to be formed, in which case the back side of the top sheet 22 is adhered to the intermediate sheet 25 over the entire surface.

Figure 15:
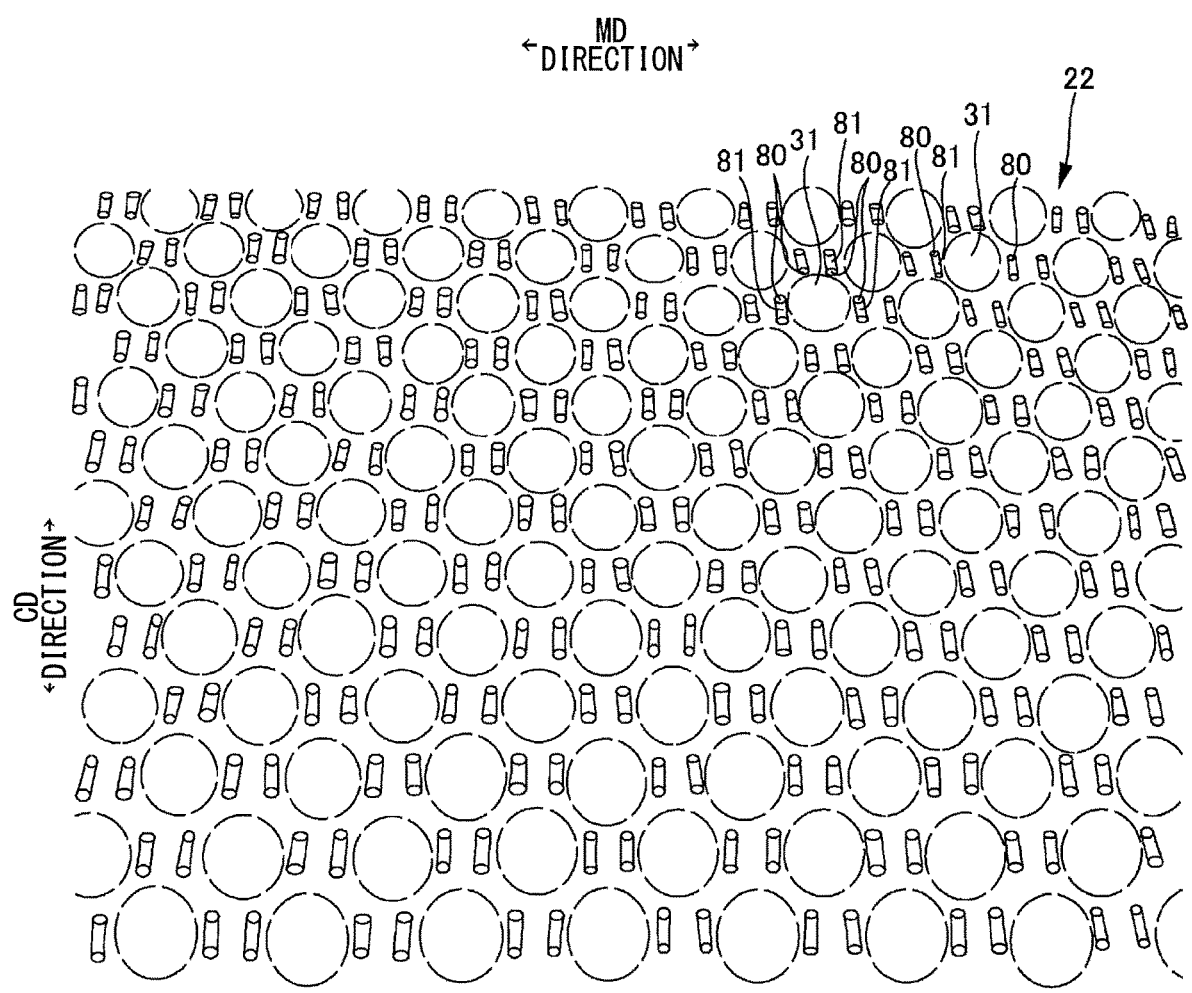
FIG. 15 is a schematic view from substantially the upper side of an assembly of a top sheet and a second sheet.
Figure 16:
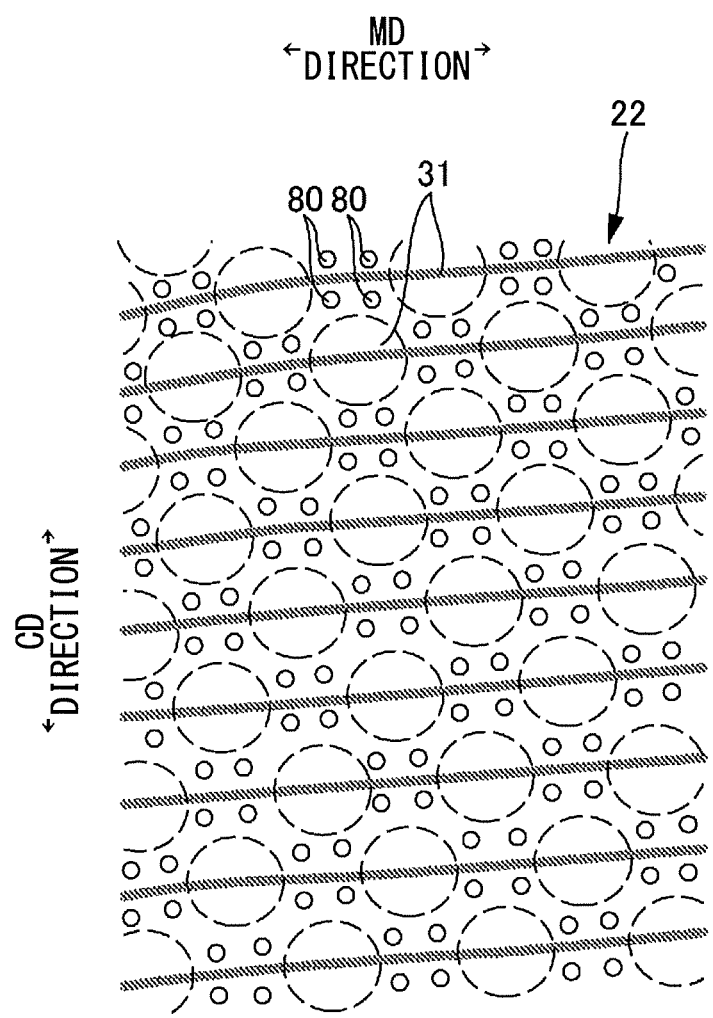
FIG. 16 is a schematic view of the top sheet surface of a comparative sample.

A sample of an assembly of the top sheet 22 and the intermediate sheet 25 adopting the patterns illustrated in FIGS. 10 and 12 (b) is illustrated in FIG. 15. By adopting the above-described characteristic joining pattern between the protruding portions 31 adjacent to each other in the MD direction, as is clear from the comparison between the sample illustrated in FIG. 15 and the sample illustrated in FIG. 16, even if vertical creases are formed when forming the protruding portions 31, the low permeation portions 80 formed by pressure welding and the compression portions 81 compressed without welding are alternately continuously formed in the CD direction, so as to traverse the vertical creases when joining with the intermediate sheet 25, and therefore the low permeation portions 80 can be formed in a state where the vertical creases are stretched to a greater extent, and this state or a state close to this state is maintained even after manufacturing. Nevertheless, the portions to be joined are intermittent in the CD direction, and therefore degrading of the flexibility and deterioration of appearance can be prevented. On the other hand, in a comparative sample having the low permeation portions 80 that do not satisfy the above conditions, many creases along the MD direction are formed with intervals in the CD direction, and the appearance is deteriorated.

The joining pattern is not particularly limited as long as a plurality of the low permeation portions 80 are arranged with intervals in the CD direction, and the low permeation portions 80 are connected in the CD direction by an interval portion that is the compression portion 81, in the region between the protruding portions 31 adjacent to each other in the MD direction. As illustrated in FIG. 11 (b) and FIG. 12 (a), when the low permeation portion 80 is formed at the center position in the CD direction corresponding to the center portion in the CD direction of the protruding portions 31 adjacent to each other in the MD direction, it is preferable in terms of preventing creases; however, as illustrated in FIG. 11 (a) and FIG. 12 (b), by forming a pattern in which the low permeation portion 80 is not formed at the center position in the CD direction, it is preferable in terms of increasing flexibility. In the former case, by making the area of the low permeation portion 80 at the center position in the CD direction to be smaller than the area of the other low permeation portions 80, it is also preferable in terms flexibility.

As illustrated in FIG. 11, in a region between the protruding portions 31 adjacent to each other in the MD direction, one row in which a plurality of the low permeation portions 80 are arranged with intervals in the CD direction is provided; in another case, as illustrated in FIGS. 10 and 12, a plurality of rows may be provided with intervals in the MD direction. The former is suitable for a pattern in which the protruding portions 31 are arranged with narrow intervals in the MD direction as in embodiment illustrated in FIG. 11 in which the protruding portions 31 are arranged in a matrix, and the latter is suitable for a pattern in which the protruding portions 31 are arranged with wide intervals in the MD direction as in embodiment illustrated in FIGS. 10 and 12 in which the protruding portions 31 are arranged in a staggered arrangement. Note that in the latter embodiment, in the interval portion between the low permeation portions 80 in the MD direction, the top sheet 22 and the intermediate sheet 25 may not be welded to each other and may be compressed similar to the interval portion in the CD direction; however, if the top sheet 22 and the intermediate sheet 25 are not welded to each other and the top sheet 22 is not compressed as much as the interval portions in the CD direction (also including non-compressed portions that are not compressed at all), it is possible to attain more excellent flexibility and appearance.

The sizes of the low permeation portions 80 in the embodiment illustrated in FIGS. 11 and 12 may be appropriately defined; however, point joining portions are preferably formed, in which each of the low permeation portions 80 between the protruding portions 31 adjacent to each other in the MD direction are formed such that the MD direction length 80$m$ is approximately 0.1 to 0.4 times (in typical cases, 0.5 mm to 3 mm, for example) the size of an MD direction center interval 31$y$ of CD direction rows of the protruding portions 31 adjacent to each other in the MD direction; and the CD direction length 80$c$ is approximately 0.1 to 0.4 times (in typical cases, 0.5 mm to 3 mm, for example) the size of a CD direction center interval 31$x$ of MD direction rows of the protruding portions 31 adjacent to each other in the CD direction. Furthermore, a CD direction interval 80$d$ of the low permeation portions 80 adjacent to each other in the CD direction is preferably approximately 1 to 5 times (in typical cases, 0.5 mm to 15 mm, for example) the size of a CD direction length 80$c$ of the low permeation portion 80, and the number of the low permeation portions 80 in the CD direction row is preferably approximately 2 to 4 portions.

On the other hand, as illustrated in FIG. 12, when the protruding portions 31 are arranged in a staggered arrangement, the interval between the protruding portions 31 adjacent to each other in the CD direction is also the interval between the protruding portions 31 adjacent to each other in the MD direction, and therefore the same low permeation portions 80 as those between the protruding portions 31 adjacent to each other in the MD direction, are provided between the protruding portions 31 adjacent to each other in the CD direction. However, as illustrated in FIG. 11, when the protruding portions 31 are arranged in a matrix, the low permeation portions 80 are intermittently provided in the MD direction between the protruding portions 31 adjacent to each other in the CD direction, different from the low permeation portions 80 between the protruding portions 31 adjacent to each other in the MD direction. The pattern of the low permeation portions 80 between the protruding portions 31 adjacent to each other in the CD direction is not particularly limited; however, it is preferable to arrange the low permeation portions 80 in the form of points with intervals in the MD direction. As illustrated in FIG. 11 ($b$), also in the interval portions in the MD direction, the compression portions 81 may be formed, similar to the interval portions in the CD direction. The row of the low permeation portions 80 in the MD direction may be arranged by providing one row at the center position of the protruding portions 31 adjacent to each other in the CD direction as illustrated, or a plurality of rows may be provided with intervals in the CD direction. Although the size of the point-like low permeation portion 80 is not particularly limited, it is preferable that the MD direction length 80$m$ is approximately 0.1 to 0.4 times (in typical cases, 0.5 mm to 3 mm, for example) the size of the MD direction center interval 31$y$ of the CD direction rows of the protruding portions 31 adjacent to each other in the MD direction, and the CD direction length 80$c$ is approximately 0.1 to 0.4 times (in typical cases, 0.5 mm to 3 mm, for example) the size of the CD direction center interval 31$x$ of the MD direction rows of the protruding portions 31 adjacent to each other in the CD direction.

The low permeation portions 80 in the embodiments illustrated in FIGS. 11 and 12 are formed in an intermittent joining pattern in the width direction and in the front-back direction, and the interval in each direction may be appropriately defined; however, for example, a CD direction joining range A3 formed by the low permeation portions 80 between the protruding portions 31 adjacent to each other in the MD direction is preferably approximately 0.3 to 1 times (in typical cases, 1 mm to 10 mm, for example) the size of a CD direction center interval 31$x$ of the MD direction rows of the protruding portions 31 adjacent to each other in the CD direction, and furthermore, an MD direction joining range A4 formed by the low permeation portions 80 between the protruding portions 31 adjacent to each other in the CD direction is preferably approximately 0.3 to 1 times (in typical cases, 1 mm to 10 mm, for example) the size of the MD direction center interval 31$y$ of the CD direction rows of the protruding portions 31 adjacent to each other in the MD direction. If the CD direction joining range A3 and the MD direction joining range A4 are too wide, the state will not be different from a state in which the low permeation portions 80 are continuously provided in the CD direction and the MD direction, and there is a possibility that the permeability and flexibility of the top sheet 22 decreases.

Figure 14:
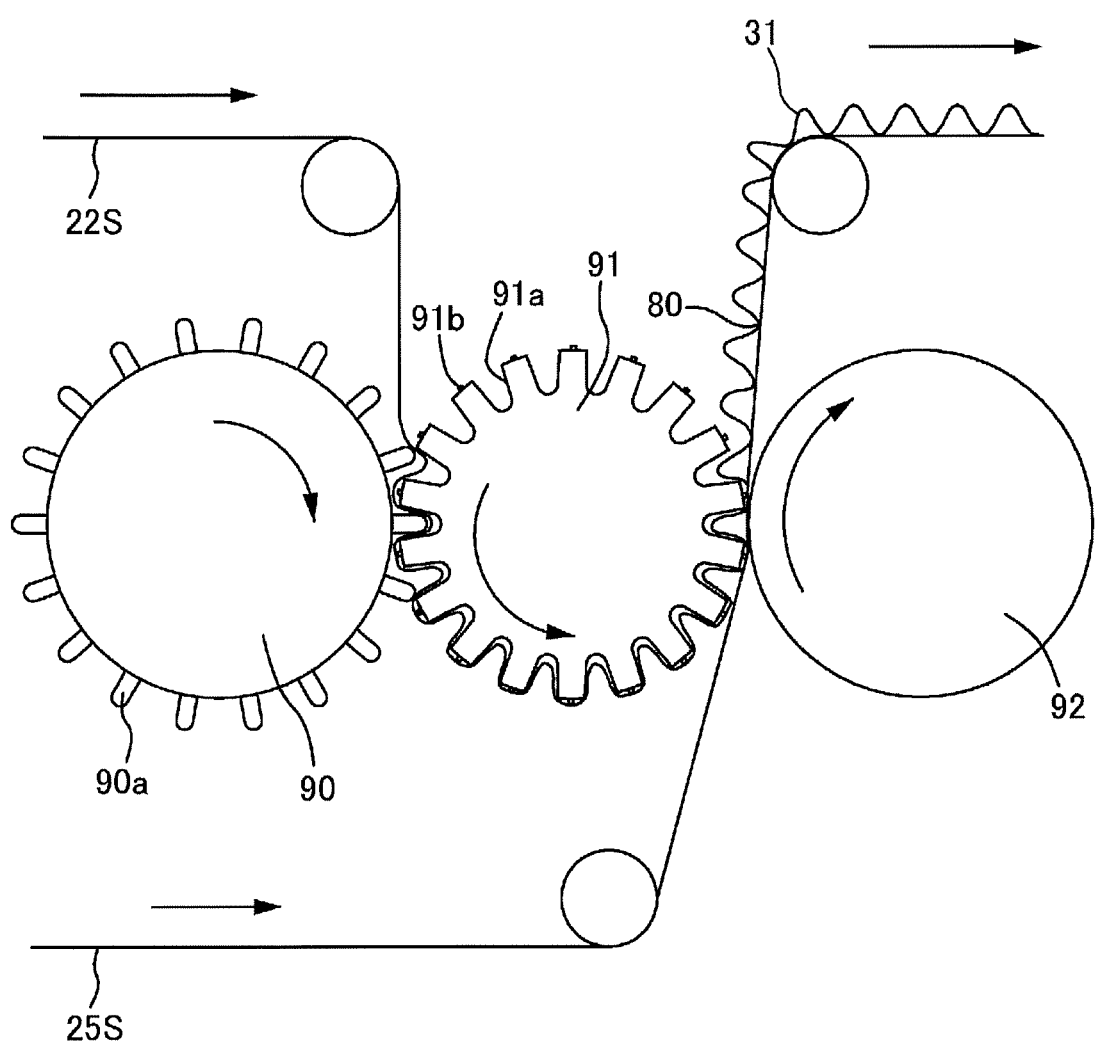
FIG. 14 is an explanatory diagram of an example of an assembly equipment of a top sheet and a second sheet.

FIG. 14 illustrates a processing facility for forming the protruding portions 31 and the low permeation portions 80 and for joining the top sheet 22 and the intermediate sheet 25. That is, this facility includes a push-in roll 90, a recessed roll 91 facing the push-in roll 90, and a joining roll 92 facing the recessed roll 91.

Figure 17:
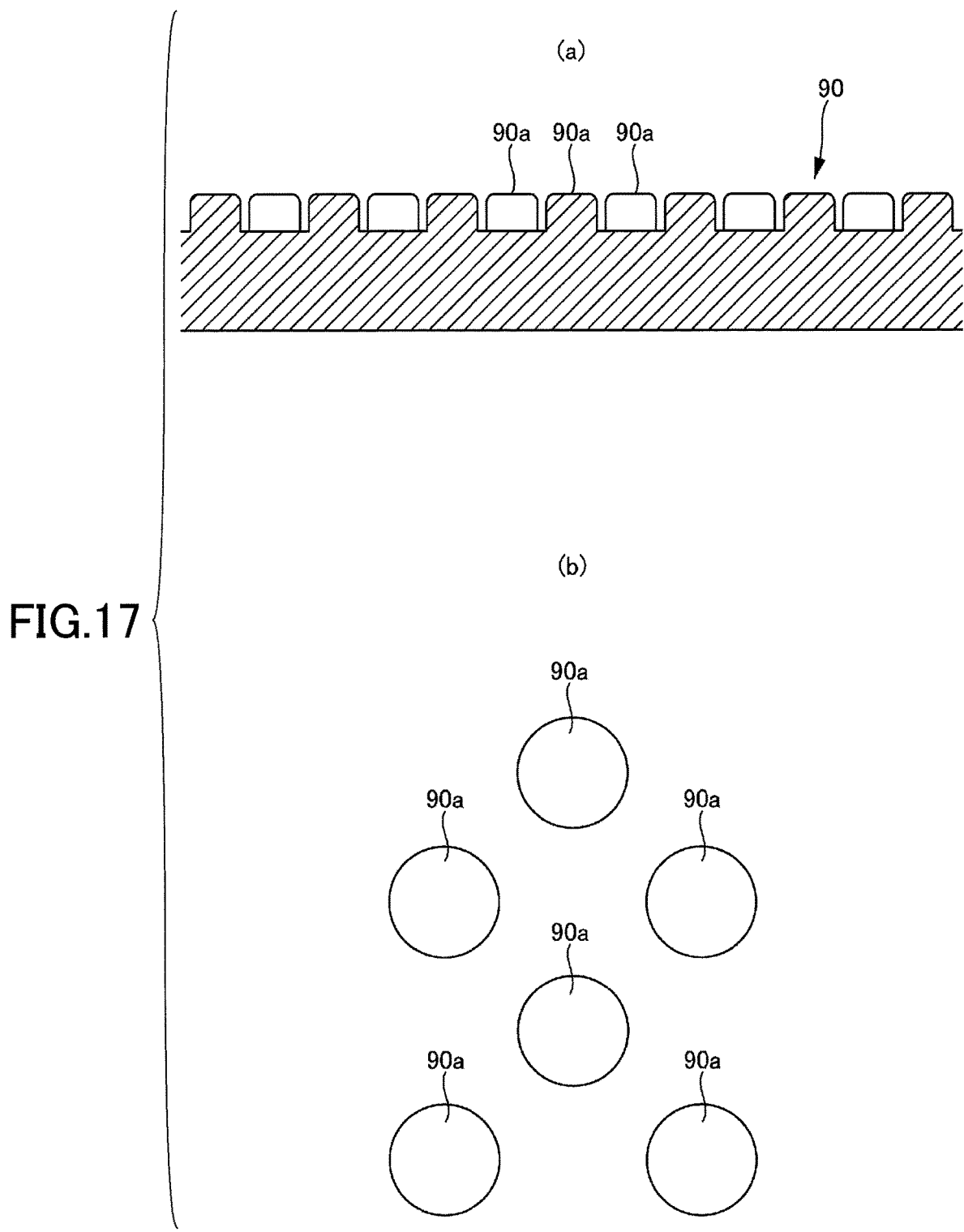
FIG. 17 is (a) a cross-sectional view of a main part and (b) an open plan view of a circumferential surface of a push-in roll.

As illustrated in FIG. 17, the push-in roll 90 has a large number of push-in protrusions 90$a$ formed on the circumferential surface, in the arrangement pattern of the protruding portions 31 described above. The shape of the protrusions of the push-in roll 90 may be appropriately defined; however, it is preferable that the shape of the protrusions of the push-in roll 90 is a truncated conical shape having a cross-section (for example, a circle, an ellipse, and a regular polygon, etc.) adapted to the shape of the protruding portion 31 to be formed.

Figure 18:
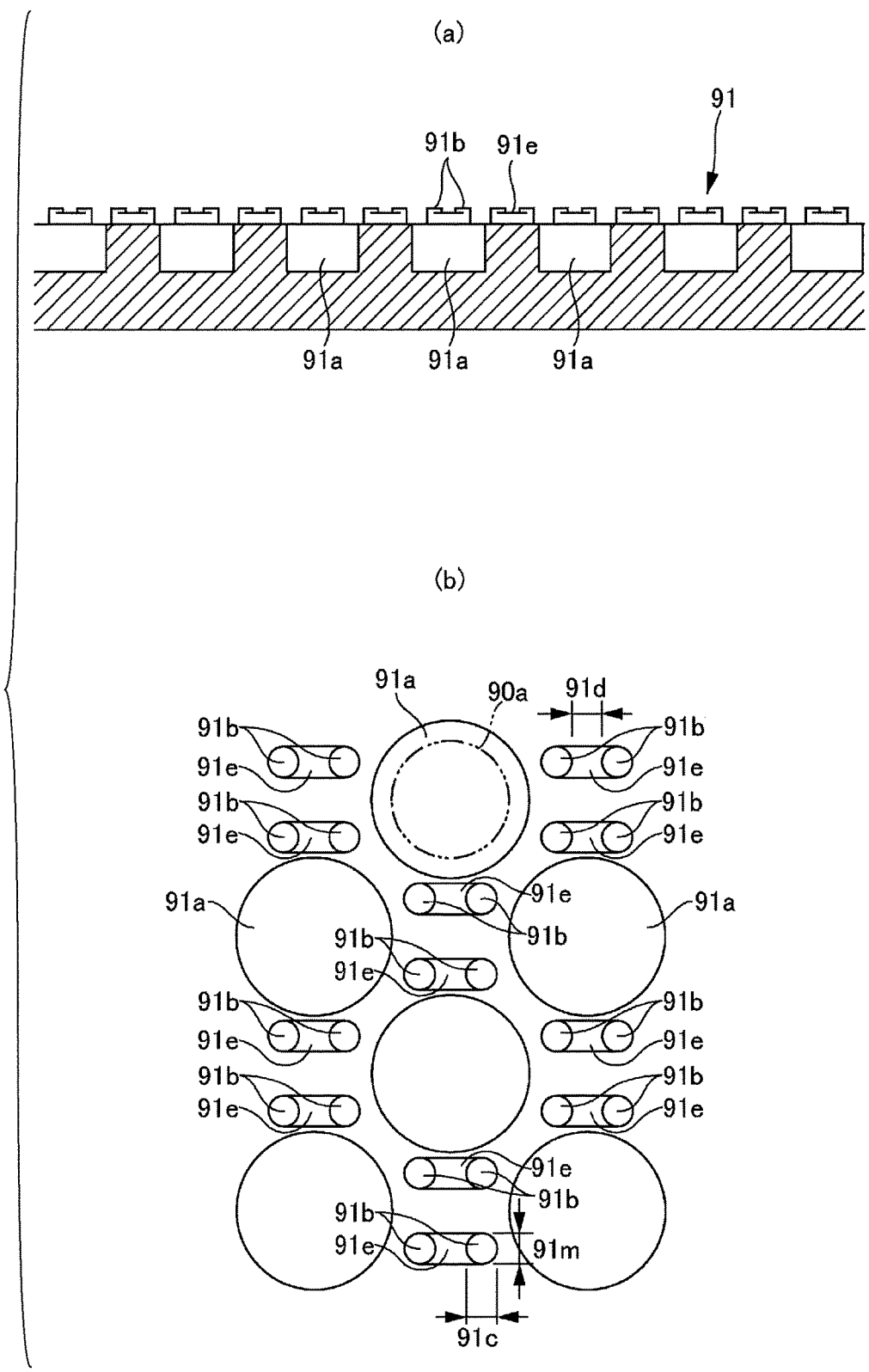
FIG. 18 is (a) a cross-sectional view of a main part and (b) an open plan view of a circumferential surface of a recessed roll.

As illustrated in FIG. 18, the recessed roll 91 is provided with push-in recesses 91$a$ on the peripheral surface, corresponding to the push-in protrusions 90$a$ of the push-in roll 90, and joining protrusions 91$b$ and compression protrusions 91$e$ are provided between the push-in recesses 91$a$. The joining protrusions 91$b$ are portions for forming the low permeation portions 80 in the above-mentioned joining pattern, and the compression protrusions 91$e$ are portions for compressing a nonwoven fabric 22S to be the top sheet 22 in the thickness direction, without welding the top sheet 22 and an intermediate sheet material 25S, at the interval portion in the CD direction of the low permeation portions 80. When the intermediate sheet material 25S is a material that is compressed in the thickness direction like a nonwoven fabric, it is obvious that the intermediate sheet 25 is also compressed at the same time by these compression protrusions 91$e$. More specifically, in the recessed roll 91, in a region between the push-in recesses 91$a$ adjacent to each other in the circumferential direction of the roll, a row in which a plurality of the joining protrusions 91$b$ are arranged with intervals in the roll axis direction, is formed so as to traverse the center position in the roll axis direction of the region, and the interval portions in the roll axis direction between the joining protrusions 91$b$ are the compression protrusions 91$e$. The portions other than the joining protrusions 91$b$, the compression protrusions 91$e$, and the push-in recesses 91$a$ are portions that do not compress the material;

however, these elements may be made to perform compression by the same degree as or by a lower degree than that by the compression protrusions 91e. As long as the protruding portions can be formed, the push-in recesses 91a of the recessed roll 91 may be a "hole" that has no bottom face and that has a size in which the push-in protrusions can enter, and the "push-in recesses 91a" has a meaning that includes such a "hole".

The size, shape, and arrangement of the push-in protrusions 90a in the push-in roll 90 correspond to the inner space size, shape, and arrangement of the protruding portions 31 to be formed, and the size, shape, and arrangement of the push-in recesses 91a in the recessed roll 91 correspond to the outer size, shape, and arrangement of the protruding portions 31 to be formed. Furthermore, the size, shape, and arrangement of the joining protrusions 91b in the recessed roll 91 correspond to the size, shape, and arrangement of the low permeation portions 80 to be formed, and the size, shape, and arrangement of the compression protrusions 91e in the recessed roll 91 correspond to the size, shape, and arrangement of the compression portions 81 when the compression portions 81 are formed. Therefore, these sizes, shapes, and arrangements, may be changed, similar to the size, shape, and arrangement of the protruding portions 31, the low permeation portions, and the compression portions described above in the section on the disposable diaper. For example, an MD direction length 91m, a CD direction length 91c, and a CD direction interval 91d of the compression protrusions 91e in the configuration illustrated in FIG. 18 (b), may be in the same ranges as those of the MD direction length 80 m, the CD direction length 80c, and the CD direction interval 80d of the low permeation portions 80 in the embodiment illustrated in FIG. 12 (b).

Figure 19:
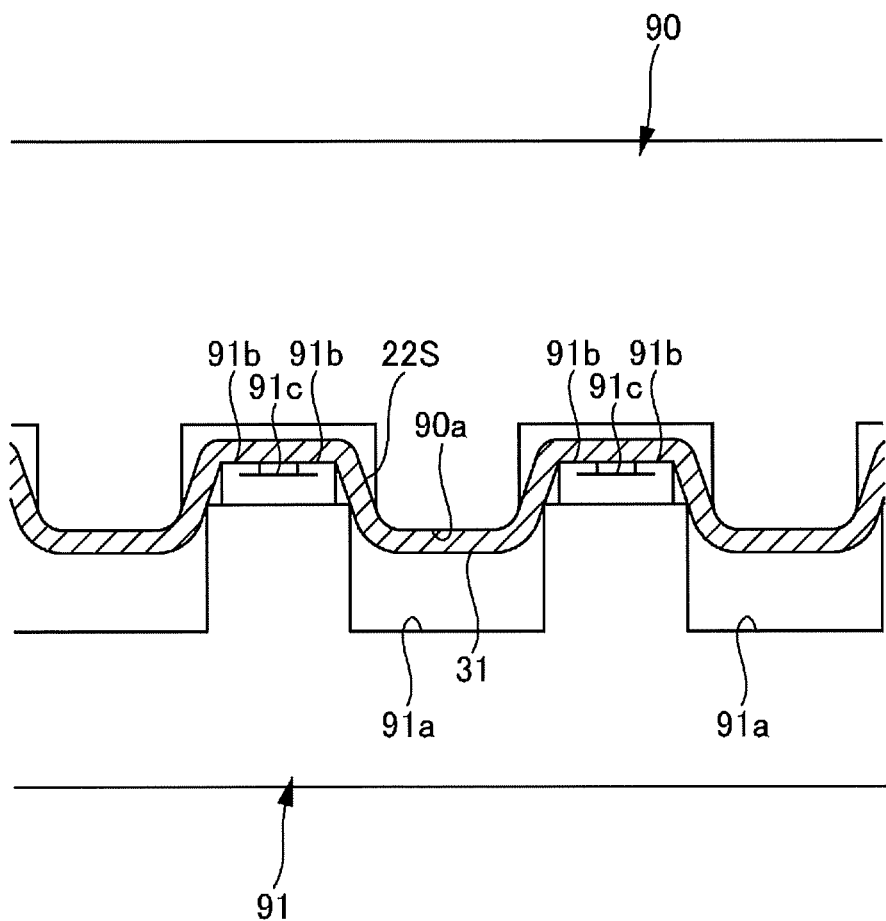
FIG. 19 is an enlarged cross-sectional view of a main part showing a process of forming protruding portions by a push-in roll and a recessed roll.

In processing, the nonwoven fabric 22S to be the top sheet 22 is transferred by tension from the downstream side of the production line, and is sandwiched between the push-in roll 90 and the recessed roll 91 as illustrated in FIG. 19, and by embossing by pushing the protrusions of the push-in roll 90 into the push-in recesses 91a of the recessed roll 91, the protruding portions 31 are formed.

Figure 20:
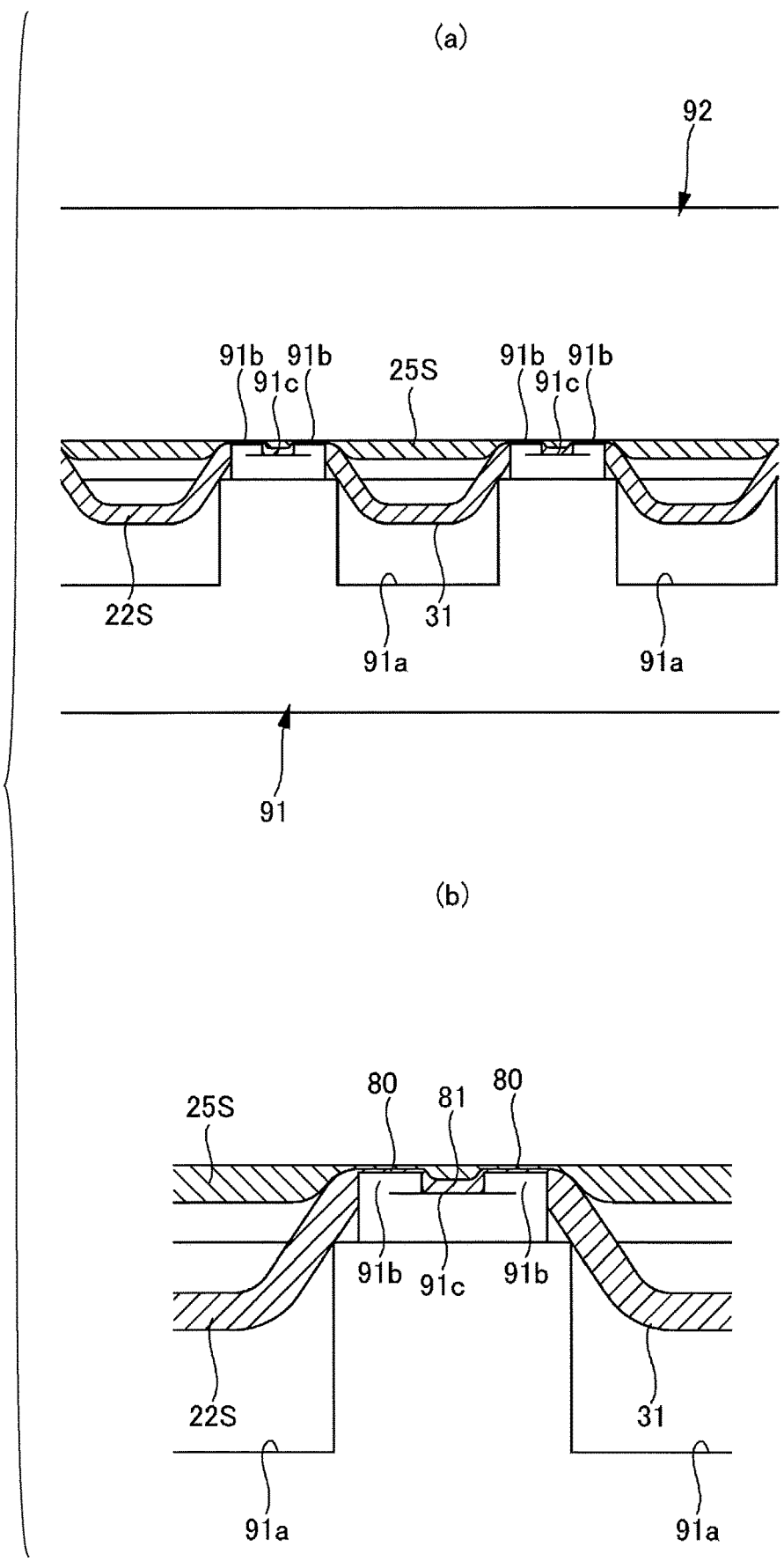
FIG. 20 is an enlarged cross-sectional view of a main part showing a joining process with a recessed roll and a joining roll.

Thereafter, in the process of guiding the nonwoven fabric 22S having the protruding portions 31 formed thereon by directly winding the nonwoven fabric 22S around the recessed roll 91, the intermediate sheet material 25S is sent onto the outside of the nonwoven fabric to be the top sheet 22 by pulling the intermediate sheet material 25S from the downstream side of the production line, and as illustrated in FIG. 20, the nonwoven fabric 22S to be the top sheet 22 and the intermediate sheet material 25S are sandwiched between the recessed roll 91 and the joining roll 92, and the nonwoven fabric 22S and the intermediate sheet material 25S are compressed between the compression protrusions 91e of the recessed roll 91 and the peripheral surface of the joining roll 92, so as to be pressure welded between the joining protrusions 91b of the recessed roll 91 and the peripheral surface of the joining roll 92, to form the low permeation portions 80, and an assembly of the top sheet 22 and the intermediate sheet 25 is manufactured. Accordingly, at the time of forming the protruding portions 31, even when vertical creases are formed between the protruding portions 31 adjacent to each other in the MD direction of the nonwoven fabric 22S to be the top sheet 22, at the time of joining the nonwoven fabric 22S with the intermediate sheet material 25S, the low permeation portions 80 and the compression portions 81 that are compressed without welding are alternately continuously formed in the CD direction, so as to traverse the vertical creases, and therefore the low permeation portions 80 can be formed in a state where the vertical creases are stretched to a greater extent, and this state or a state close to this state is maintained even after manufacturing. Nevertheless, the portions to be joined are intermittent in the CD direction, and therefore degrading of the flexibility and deterioration of appearance can be prevented. As understood from this principle, not only the traces of compression by the compression protrusions 91e remain as the above-described compression portions 81, but also traces of compression do not remain almost or completely, and therefore the effect of preventing vertical creases is attained.

As the pressure-welding means, besides a heat seal for heating the roll and welding the material, an ultrasonic seal may be adopted, as long as welding is performed while compressing the material in the thickness direction. A disposable diaper can be produced by attaching assembly of the processed top sheet 22 and the intermediate sheet 25 to an absorbent body, etc., according to a known method.

As in the embodiment illustrated in FIG. 14, by a processing method of joining the top sheet 22 with the material of the intermediate sheet 25 immediately after forming the protruding portions 31 with not much time for reducing the creases, the creases tend to remain easily, and therefore the above-described joining pattern is preferably adopted. As a matter of course, as long as the low permeation portions 80 are formed after the protruding portions 31 are formed by emboss processing, the processing facility is not limited to the above-described processing facility with three rolls. Furthermore, in the illustrated example, a nonwoven fabric to be the top sheet 22 is sent directly to the position where the push-in roll 90 and the recessed roll 91 mesh with each other; however, the nonwoven fabric to be the top sheet 22 may be wound only around the push-in roll 90 from the tangential direction of the circumferential surface of the push-in roll 90, and after sandwiching the nonwoven fabric between the push-in roll 90 and the recessed roll 91, the nonwoven fabric may be guided to the circumferential surface of the recessed roll 91.

Absorption Rate Test

Based on the structure of the pad type disposable diaper illustrated in FIGS. 1 to 4, samples were manufactured, that were different in terms of the presence or absence of the low permeation portions 80 of the top sheet 22, the pattern of the low permeation portions 80, and the absorbable capacity, and an absorption rate test was performed.

Example 1

The upper layer absorbent body 23A was a mixed stacked fiber body of pulp fibers and high-absorbent polymer particles, the basis weight of the pulp fibers was 351 g/m$^2$, the basis weight of the high-absorbent polymer particles was 242 g/m$^2$, and the thickness was 5.0 mm. The overall length of the upper layer absorbent body 23A was 480 mm, and the overall width of the upper layer absorbent body 23A was 140 mm.

The high-absorbent polymer particles used in the upper layer absorbent body 23A had the following features. Specifically, when the particles are sieved (shaking for 5 minutes) by using a standard sieve of 500 μm (JIS Z8801-1:2006) having a water absorption rate of 38 seconds and a water absorption amount of 73 g/g, and the particles dropped by the above sieving are sieved (shaking for 5 minutes) by using a standard sieve of 180 μm (JIS Z8801-1:2006), the proportion of particles remaining on the standard sieve of 500 µm is 50% by weight or less, and the proportion of particles remaining on the standard sieve of 180 µm is 50% by weight or more.

The slit 40 of the upper layer absorbent body 23A was extended backward from the front end of the upper layer absorbent body 23A from the position of 25 mm to the position of 240 mm, and the width 40W of the slit 40 was 20 mm and an interval 40D between the left and right slits 40 was 25 mm.

The lower layer absorbent body 23B was a mixed stacked fiber body of pulp fibers and high-absorbent polymer particles, the basis weight of the pulp fibers was 245 g/m$^2$, the basis weight of the high-absorbent polymer particles was 91.7 g/m$^2$, and the thickness was 3.6 mm. The total length of the lower layer absorbent body 23B was 570 mm, and the total width of the lower layer absorbent body 23B was 260 mm.

The high-absorbent polymer particles used in the lower layer absorbent body 23B had the following features. Specifically, when the particles are sieved (shaking for 5 minutes) by using a standard sieve of 500 µm (JIS Z8801-1: 2006) having a water absorption rate of 28 seconds and a water absorption amount of 60 g/g, and the particles dropped by the above sieving are sieved (shaking for 5 minutes) by using a standard sieve of 180 µm (JIS Z8801-1:2006), the proportion of particles remaining on the standard sieve of 500 µm is 25% by weight or less, and the proportion of particles remaining on the standard sieve of 180 µm is 70% by weight or more.

The packaging sheet was crepe paper with a basis weight of 15 g/m$^2$.

The top sheet was a hydrophilic two-layer air-through nonwoven fabric having a basis weight of 21 g/m$^2$ and a thickness of 0.15 mm, the upper layer fiber was a core-in-sheath type conjugate fiber (core PP, sheath PE) of 2.2 dtex, and the lower layer fiber was a core-in-sheath type conjugate fiber (core PET, sheath PE) of 4.4 dtex.

The intermediate sheet 25 was a hydrophilic air-through nonwoven fabric having a basis weight of 22 g/m$^2$ and a thickness of 0.14 mm, using a core-in-sheath type conjugate fiber (core PET, sheath PE) having a thickness of 2.2 dtex.

The top sheet 22 and the intermediate sheet 25 were joined by the manufacturing method illustrated in FIG. 14, and by this joining, the region 11 having the low permeation portions 80 of the pattern illustrated in FIG. 21 (*a*) was formed over the entire region including the intermediate sheet 25.

Example 2

Example 2 was the same as example 1, except that the pattern of the low permeation portions 80 was the pattern illustrated in FIG. 21 (*b*).

Example 3

Figure 22:
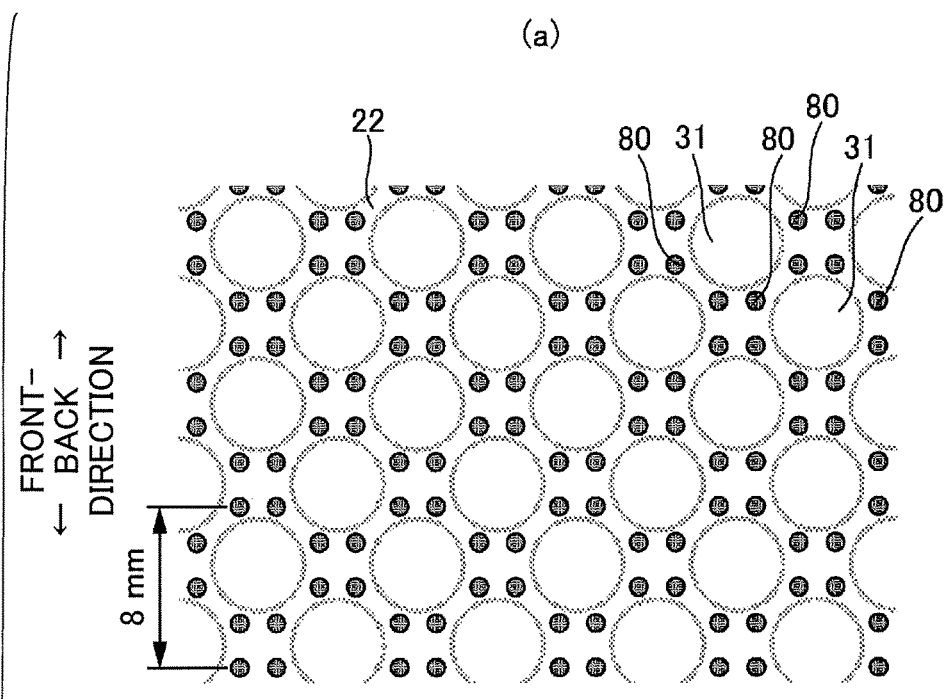
FIG. 22 is an enlarged plan view of a pattern of low permeation portions.
Figure 22:
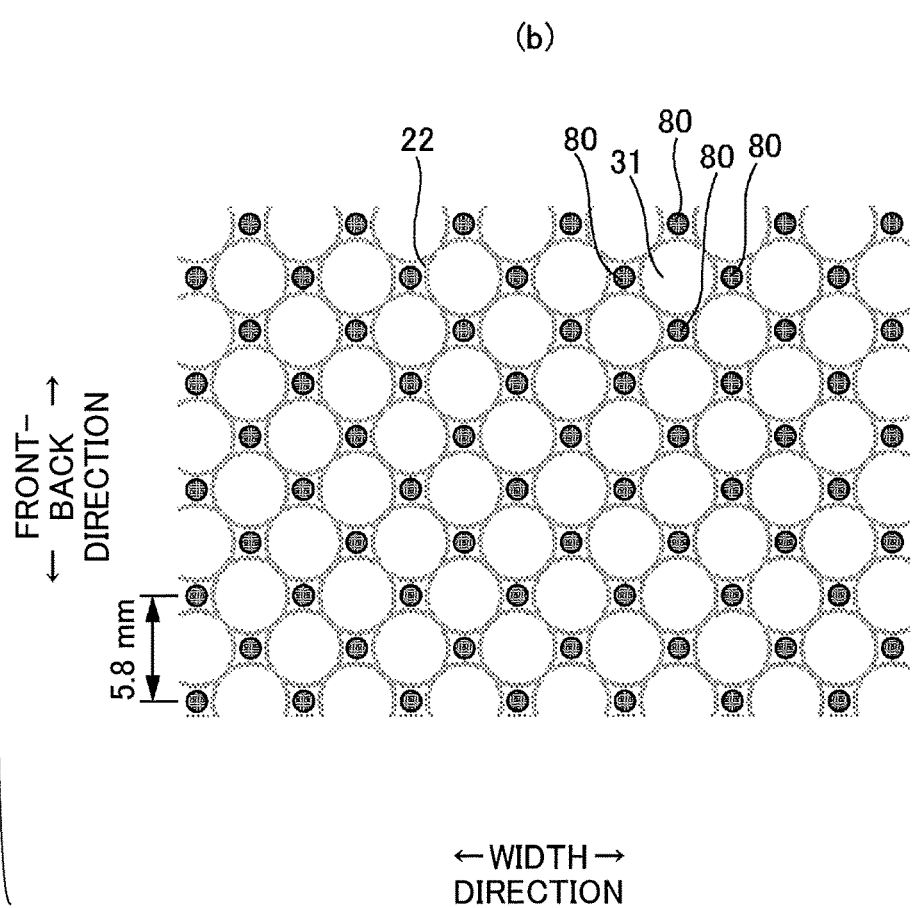

Example 3 was the same as example 1, except that the pattern of the low permeation portions 80 was the pattern illustrated in FIG. 22 (*a*).

Example 4

Example 4 was the same as example 1, except that the pattern of the low permeation portions 80 was the pattern illustrated in FIG. 22 (*b*).

Comparative Example 1

With respect to the upper layer absorbent body 23A, the basis weight of the pulp fibers was set to 372 g/m$^2$, the basis weight of the high-absorbent polymer particles was set to 279 g/m$^2$, and the thickness was set to 5.3 mm; with respect to the lower layer absorbent body 23B, the basis weight of the pulp fibers was set to 246 g/m$^2$, the basis weight of the high-absorbent polymer particles was set to 91.0 g/m$^2$, and the thickness was set to 3.6 mm. Furthermore, the top sheet 22 and the intermediate sheet 25 were not joined by the manufacturing method illustrated in FIG. 14, and no low permeation portions 80 were provided at all. Otherwise, comparative example 1 was the same as example 1.

Comparative Example 2

The top sheet 22 and the intermediate sheet 25 were not joined by the manufacturing method illustrated in FIG. 14, and no low permeation portions 80 were provided at all. Otherwise, comparative example 2 was the same as example 1.

Test Method

Figure 24:
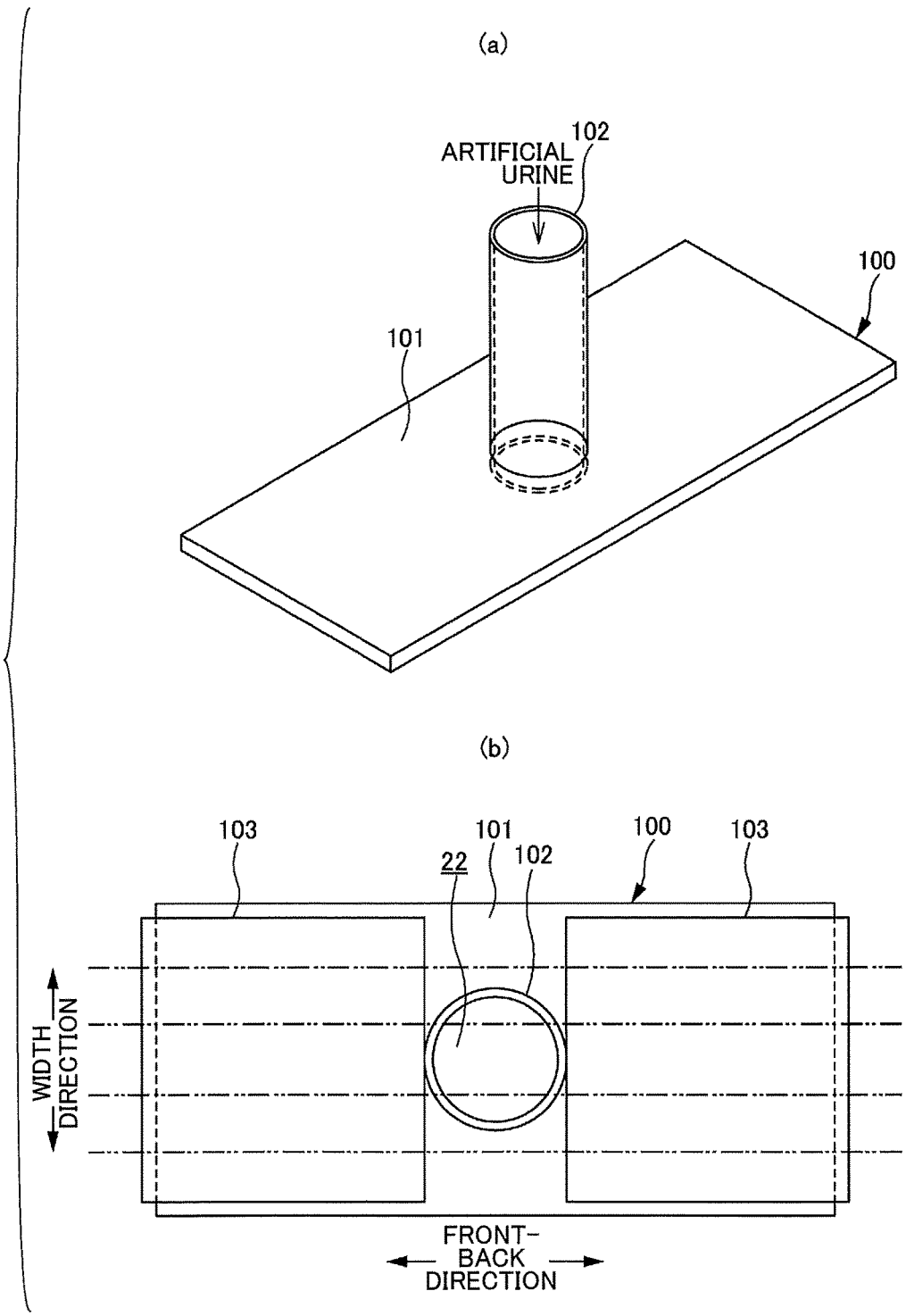
FIG. 24 is a schematic diagram of an absorption rate test.

On a horizontal table, the samples were fixed in an open state, and an injection device 100 was placed on the top sheet 22 as illustrated in FIG. 24(*b*). As illustrated in FIG. 24(*a*), the injection device 100 that was used had a base portion 101 made of a flat plate having a length of 240 mm and a width of 110 mm, and a cylindrical portion 102 having an inner diameter of 44 mm and a height of 120 mm that passes through the center of the base portion 101 and that is open at the bottom surface of the base portion 101. In the test, as illustrated in FIG. 24(*b*), the center of the cylindrical portion 102 of the injection device 100 was positioned at the center in the front-back direction and at the center in the width direction in the region between the two slits 40, the base portion 101 was placed downward such that the longitudinal direction of the base portion 101 is in the front-back direction of the sample, and weights 103 having a square bottom surface of 10 cm×10 cm and a weight of 0.5 kg were placed on both sides in the longitudinal direction of the base portion 101. Then, 150 ml of artificial urine having a temperature of 37 degrees was poured at once from the upper end inlet of the cylindrical portion 102, and the time (seconds) from the start of pouring the artificial urine until the artificial urine is completely absorbed (until there is no artificial urine on the top sheet 22) was measured by manually operating a stopwatch. The measurement was performed three times, and the average value was taken as the absorption rate.

Test Results

Figure 25:
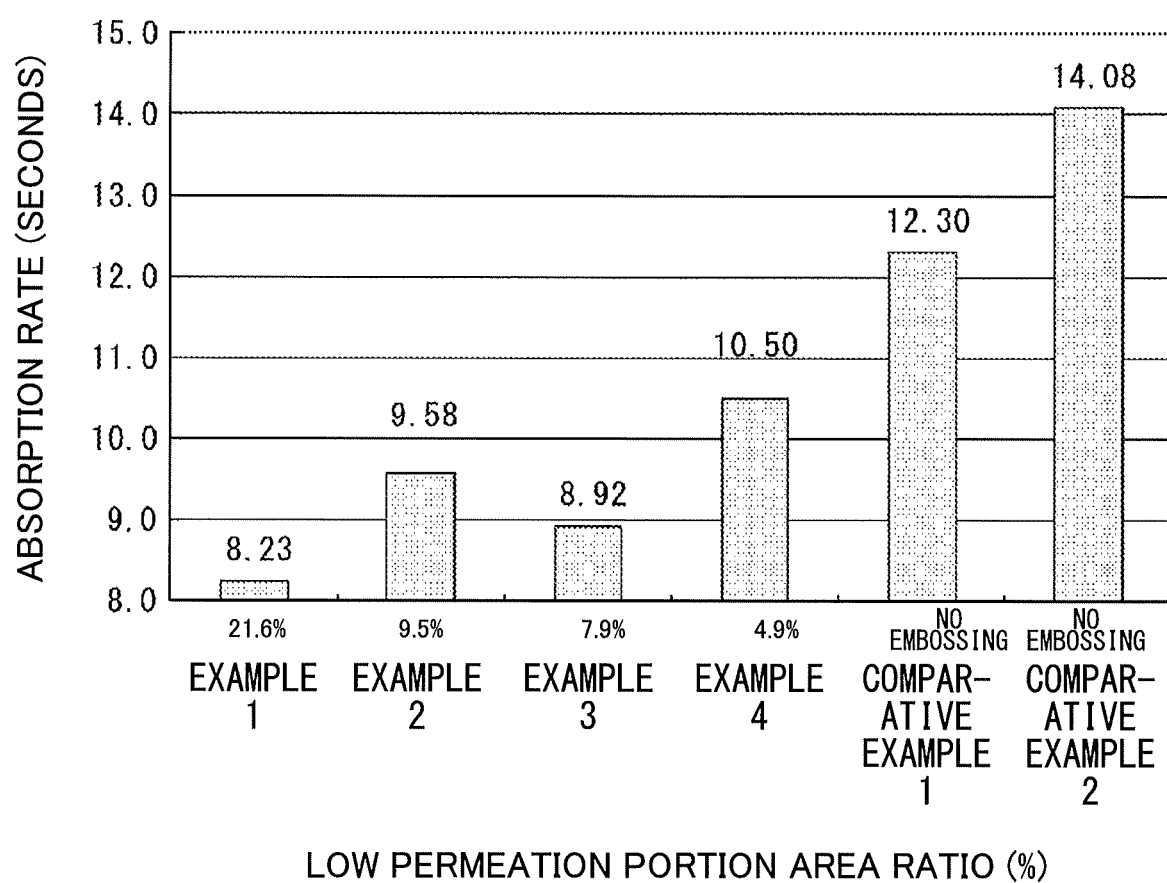
FIG. 25 is a graph of test results.

The test results are illustrated in FIG. 25. It was found that the absorption rates of examples 1 to 4 according to the present invention were superior to those of comparative examples 1 and 2.

Explanation of Terms in Specification

When the following terms are used in the specification, the terms have the following meanings unless otherwise specified in the specification.

"Front-back (longitudinal) direction" means a direction connecting the stomach side (front side) and the back side (rear side), and "width direction" means a direction (right-left direction) orthogonal to the front-back direction.

"Open state" means a state in which the diaper is flatly opened without shrinkage or slackness.

"Elongation rate" means the value when the natural length is taken as 100%.

"Basis weight" is measured as follows. After preliminarily drying the sample or test piece, the sample or test piece is left in a test chamber or a device in a standard state (the test location has a temperature of 20±5° C. and a relative humidity of 65% or less), such that the sample or test piece has a constant mass. Preliminary drying refers to making a sample or a test piece have a constant mass in an environment having a relative humidity of 10% to 25% and not exceeding a temperature of 50° C. Note that for fibers with official moisture regain of 0.0%, preliminary drying may not be performed. By using a unit weight plate (200 mm×250 mm, ±2 mm) cut from the test piece having the constant mass, a sample having a size of 200 mm×250 mm (±2 mm) is cut out. The weight of the sample is measured, and the weight is multiplied by 20 to calculate the weight per square meter, thereby obtaining the basis weight.

"Thickness" of the top sheet 22 and the intermediate sheet 25 illustrated in FIGS. 10 to 20 means the apparent thickness, and is measured by the method described in paragraph [0017] of Japanese Patent No. 3611838. That is, at the time of measurement, in a state where the top sheet 22 and the intermediate sheet 25 are joined, a measurement piece of 30 mm in length×30 mm in width is cut out. Then, a cut surface is formed by a line substantially parallel to the longitudinal direction [the fiber orientation direction (flow direction when manufacturing nonwoven fabric) of the nonwoven fabric (fiber assembly) constituting the top sheet 22] and passing through the low permeation portions 80. An enlarged photograph of the cut surface is taken using a Digital Microscope VHX-1000, manufactured by Keyence Corporation, and the apparent maximum thickness of the top sheet 22 is obtained based on the enlarged photograph, and this thickness is taken as the thickness of the top sheet 22, and the apparent thickness of the intermediate sheet 25 is measured at the measurement portion of the maximum thickness of the top sheet 22, and this thickness is taken as the thickness of the intermediate sheet 25. Furthermore, the size in the cross-sectional direction such as the thickness of the other portions (the thickness of the low permeation portions 80 and the thickness of the compression portions 81, etc.) and a height 31z of the protruding portions 31, etc., is obtained by measuring the height of the protuberance from the bottom to the top of the protruding portion, in a similar manner as measuring the "thickness" of the top sheet and the intermediate sheet.

The "thickness" of the absorbent body is measured by using a thickness measuring instrument manufactured by OZAKI MFG. CO., LTD. (Peacock, large type dial thickness gauge, model J-B (measurement range 0 mm to 35 mm) or model K-4 (measurement range 0 mm to 50 mm)), by laying the sample and the thickness measuring instrument in a horizontal manner.

The "thickness" other than the above is automatically measured by an automatic thickness measuring instrument (KES-G 5 handy compression measuring program) under the conditions of a load of 10 gf/cm$^2$ and a pressure area of 2 cm$^2$.

The water absorption amount is measured according to JIS K7223-1996 "Test method of water absorption amount of high-absorbent resin".

The water absorption rate is the "time to the end point" when JIS K7224-1996 "Test method of water absorption amount of high-absorbent resin" is carried out using 2 g of high-absorbent polymer and 50 g of physiological saline.

"Artificial urine" was prepared by mixing urea: 2 wt %, sodium chloride: 0.8 wt %, calcium chloride dihydrate: 0.03 wt %, magnesium sulfate heptahydrate: 0.08 wt %, ion exchanged water: 97.07 wt %, and is used at a temperature of 40° C., unless otherwise specified.

In the absence of descriptions on environmental conditions in tests and measurements, the tests and measurements are carried out in a test chamber or a device in a standard state (the test location has a temperature of 20±5° C. and a relative humidity of 65% or less).

The size of each part means the size in the open state, not the natural length state, unless otherwise stated.

INDUSTRIAL APPLICABILITY

Although the present invention is suitable for a pad type disposable diaper as in the above example, the present invention can also be used for disposable diapers of other forms such as a pants type or a tape type disposable diaper.

REFERENCE SIGNS LIST

B2 . . . back side portion, C2 . . . crotch portion, F2 . . . front side portion, 11 . . . region including low permeation portions, 21 . . . liquid impermeable sheet, 22 . . . top sheet, 23A, 23B . . . absorbent bodies, 24 . . . three-dimensional gather, 24s . . . gather sheet, 25 . . . intermediate sheet, packaging sheet, 27 . . . exterior sheet, 30 . . . depressed portion, 31 . . . protruding portions, slit, 41 . . . other slit, 200 . . . pad type disposable diaper, 80 . . . low permeation portions, 23A . . . upper layer absorbent body, 23B . . . lower layer absorbent body.

The invention claimed is:

1. A disposable diaper comprising:
   a crotch portion;
   a front side portion extending to a front side of the crotch portion;
   a back side portion extending to a back side of the crotch portion;
   an absorbent body provided in a range including the crotch portion in a front-back direction;
   a top sheet covering a front surface of the absorbent body; and
   an intermediate sheet made of a material having low water retentivity and high liquid permeability that is interposed between the top sheet and the absorbent body, wherein
   the top sheet is formed of a thermoplastic nonwoven fabric,
   the absorbent body is formed of a lower layer absorbent body and an upper layer absorbent body provided on a front surface of the lower layer absorbent body,
   a slit having a predetermined width is provided in the upper layer absorbent body at least at the crotch portion so as to extend in the front-back direction, and the slit having the predetermined width is not provided in the lower layer absorbent body,
   the top sheet includes a depressed portion that is depressed into the slit, and
   low permeation portions are provided in multiple quantities with intervals at least in the depressed portion, the low permeation portions being portions that are compressed in a thickness direction and portions where fibers of the top sheet are welded to the fibers of the intermediate sheet, and protruding portions are provided between the low permeation portions, the protruding portions protruding from a front surface of the top sheet;

being arranged at intervals in a width direction and in a front-back direction of the top sheet;

having a length in the front-back direction of the top sheet that is larger than front-back interval between the protruding portions arranged in the front-back direction; and having a width in the width direction of the top sheet that is larger than a width interval between the protruding portions arranged in the width direction.

2. The disposable diaper according to claim 1, wherein an area ratio of the low permeation portions in the depressed portion is greater than or equal to 4%.

3. The disposable diaper according to claim 1, wherein the low permeation portions, which have a shape elongated in the front-back direction, are intermittently provided in the front-back direction at intervals shorter than a length of each of the low permeation portions in the front-back direction, in the depressed portion.

4. The disposable diaper according to claim 1, wherein the low permeation portions, which have a shape that continues from a front end to a back end of a region including the low permeation portions, are provided in the depressed portion.

5. The disposable diaper according to claim 1, wherein a plurality of rows of the low permeation portions are provided with intervals in a width direction, at least in the depressed portion.

6. The disposable diaper according to claim 1, wherein
the protruding portions are arranged in a staggered arrangement, and
the width between the protruding portions arranged in the width direction is 0.5 to 0.9 times the size of the protruding portion in the width direction.

7. The disposable diaper according to claim 1, wherein
the protruding portions are arranged in a matrix, and
the width between the protruding portions arranged in the width direction is 0.1 to 0.5 times the size of the protruding portions in the width direction.

* * * * *